US005599923A

United States Patent [19]
Sessler et al.

[11] Patent Number: 5,599,923
[45] Date of Patent: Feb. 4, 1997

[54] TEXAPHYRIN METAL COMPLEXES HAVING IMPROVED FUNCTIONALIZATION

[75] Inventors: Jonathan L. Sessler, Austin, Tex.; Tarak D. Mody; Gregory W. Hemmi, both of Sunnyvale, Calif.

[73] Assignees: Board of Regents, University of TX, Austin, Tex.; Pharmacyclics, Inc., Sunnyvale, Calif.

[21] Appl. No.: 196,964

[22] Filed: Feb. 15, 1994

Related U.S. Application Data

[63] Continuation-in-part of Ser. No. 98,514, Jul. 28, 1993, and Ser. No. 135,118, Oct. 12, 1993, Pat. No. 5,457,183, which is a continuation-in-part of Ser. No. 822,964, Jan. 21, 1992, Pat. No. 5,252,720, which is a continuation-in-part of Ser. No. 771,393, Sep. 30, 1991, abandoned, which is a continuation-in-part of Ser. No. 539,975, filed as PCT/US90/01208, Mar. 6, 1990, Pat. No. 5,162,509, which is a division of Ser. No. 320,293, Mar. 6, 1989, Pat. No. 4,935,498, said Ser. No. 98,514, is a division of Ser. No. 822,964.

[51] Int. Cl.$^6$ .................................................. C07D 487/22
[52] U.S. Cl. ........................... 540/145; 540/465; 540/472
[58] Field of Search .................................. 540/145, 465, 540/472, 474

[56] References Cited

U.S. PATENT DOCUMENTS

| | | | |
|---|---|---|---|
| 4,647,447 | 3/1987 | Gries et al. | 424/9 |
| 4,878,891 | 11/1989 | Judy et al. | 604/5 |
| 4,880,008 | 11/1989 | Lauffer et al. | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,162,509 | 11/1992 | Sessler et al. | 534/15 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1984 | Sessler et al. | 204/157.5 |

FOREIGN PATENT DOCUMENTS

| | | |
|---|---|---|
| 0111418A2 | 6/1984 | European Pat. Off. . |
| 0196515A1 | 10/1986 | European Pat. Off. . |
| 0233701A2 | 8/1987 | European Pat. Off. . |
| WO90/10633 | 9/1990 | WIPO . |

OTHER PUBLICATIONS

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Acholla et al., "Binucleating Tetrapyrrole Macrocycles", *J. Am. Chem. Soc.*, 107:6902–6908, 1985.

Acholla et al., "A Binucleating 'Accordian' Tetrapyrrole Macrocycle", *Tetrahedron Lett.*, 25:3269–3270, 1984.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Abid et al., "Lanthanide Complexes of Some Macrocyclic Schiff Bases Derived from Pyridine–2,6–dicarboxaldehyde and α,ω–Primary diamines", *Inorg. Chim. Acta*, 95:119–125, 1984.

Ansell, "X–Ray Crystal Structure of the Pentagonal Bipyramidal Nickel (11) Complex [Ni$_{11}$(L) (H$_2$O)$_2$] (BF$_4$)$_2$ and the Selective Stabilisation of the Nickel (1) Oxidation State by a Quinquedentate Macrocyclic Ligand", *J. Chem. Soc., Chem. Commun.*, 546–547, 1982.

Abid et al., "Lanthanide Complexes of Some Macrocyclic Schiff Bases Derived from Pyridine–2,6–dicarboxaldehyde and α,ω–Primary diamines", *Inorg. Chim. Acta*, 95:119–125, 1984.

Basile et al., "Metal–Activated Hydrolytic Cleavage of DNA," *J. Am. Chem. Soc.*, 109:7550–7551, 1987.

Bauer et al., "Sapphyrins: Novel Aromatic Pentapyrrolic Macrocycles", *J. Am. Chem. Soc.*, 105:6429–6436, 1983.

Bradley et al., "Antisense Therapeutics," *Gene Regulation: Biology of Antisense RNA and DNA*, 285–293, 1992.

Breslow et al., "Effects of Metal Ions, Including Mg$^{2+}$ and Lanthanides, on the Cleavage of Ribonucleotides and RNA Model Compounds," *Proc. Natl. Acad. Sci. USA*, 88:4080–4083, 1991.

Broadhurst et al., "Preparation of Some Sulphur–containing Polypyrrolic Macrocycles. Sulphur Extrusion from a meso–Thiaphlorin", *J. Chem. Soc., Chem. Commun.*, 807–809, 1970.

(List continued on next page.)

*Primary Examiner*—Mukund J. Shah
*Assistant Examiner*—Pavanaram K. Sripada
*Attorney, Agent, or Firm*—Arnold, White & Durkee

[57] ABSTRACT

Texaphyrin metal complexes having improved functionalization including the addition of electron donating groups to positions 12, 15, 18 and/or 21 and/or the addition of electron withdrawing groups to positions 15 or 18 of the macrocycle. Electron donating groups at positions 12, 15, 18 and/or 21 contribute electrons to the aromatic π system of the macrocycle which stabilizes the metal complex to demetallation and the imine bonds to hydrolysis, these texaphyrin metal complexes having enhanced stability are useful for localization, magnetic resonance imaging, radiosensitization, radiation therapy, fluorescence imaging, photodynamic tumor therapy and applications requiring singlet oxygen production for cytotoxicity. Electron withdrawing groups at positions 15 or 18 render the macrocycle more readily reduced, i.e. the redox potential is lower and the macrocycle more readily gains an electron to form a radical. Such texaphyrins having a low redox potential are useful for radiosensitization applications.

34 Claims, 12 Drawing Sheets

OTHER PUBLICATIONS

Abid et al., "Lanthanide Complexes of Some Macrocyclic Schiff Bases Derived from Pyridine-2,6-dicarboxaldehyde and α,ω-Primary diamines", Inorg. Chim. Acta, 95:119–125, 1984.

Broadhurst et al., "18-and 22-π-Electron Macrocycles Containing Furan, Pyrrole, and Thiophene Rings", J. Chem. Soc., Chem. Commun., 1480–1482, 1969.

Broadhurst et al., "New Macrocyclic Aromatic Systems Related to Porphins", J. Chem. Soc., Chem. Commun., 23–24, 1969.

Broadhurst et al., "The Synthesis of 22 π-Electron Macrocycles. Sapphyrins and Related Compounds", J. Chem. Soc. Perkin Trans. 1:2111–2116, 1972.

Browne and Bruice, "Chemistry of Phosphodiesters, DNA and Models. 2. The Hydrolysis of Bis(8-hydroxyquinoline) Phosphate in the Absence and Presence of Metal Ions," *Journal of the American Chemical Society*, 114(13):4951–4958, 1992.

Chin et al., "Co(III) Complex Promoted Hydrolysis of Phosphate Diesters: Comparison in Reactivity of Rigid cis-Diaquotetraazacobalt (III) Complexes," J. Am. Chem. Soc., 111:186–190, 1989.

Chin and Banaszczyk, "Rate-Determining Complexation in Catalytic Hydrolysis of Unactivated Esters in Neutral Water," J. Am. Chem. Soc., 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$-Phosphato Bridge," J. Am. Chem. Soc., 111:4103–4104, 1989.

Chin and Zou, "Catalytic Hydrolysis of cAMP," Can. J. Chem., 65:1882–1884, 1987.

Chung et al., "Synthesis and Characterization of a Reactive Binuclear Co(III) Complex. Cooperative Promotion of Phosphodiester Hydrolysis," Tetrahedron Letters, 31(38):5413–5146, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Cuellar et al., "Synthesis and Characterization of Metallo and Metal-Free Octaalkylphthalocyanines and Uranyl Decaalkysuperphthalocyanines", Inorg. Chem., 20:3766–3770, 1981.

Day et al., "Large Metal Ion-Centered Template Reactions. A Uranyl Complex of Cyclopentakis (2-iminoisoindoline)", J. Am. Chem. Soc., 97:4519–4527, 1975.

De Cola et al., "Hexaaza Macrocyclic Complexes of the Lanthanides", Inorg. Chem., 25:1729–1732, 1986.

Dougherty, "Photosensitizers: Therapy and Detection of Malignant Tumors", Photochem. Photobiol., 45:879–889, 1987.

Furuta et al., "Phosphate Anion Binding: Enhanced Transport of Nucleotide Monophosphate Using a Sapphyrin Carrier, " J. Am. Chem. Soc., 113:6677–6678, 1991.

Gosmann et al., "Synthesis of a Fourfold Enlarged Porphyrin with an Extremely Large, Diamagnetic Ring-Current Effect", Angew. Chem., Int. Ed Engl., 25:1100–1101, 1986.

Gossauer, "Syntheses of Some Unusual Polypyrrole Macrocycles", Bull. Soc. Chim. Belg., 92:793–795, 1983.

Hanvey et al., "Antisense and Antigene Properties of Peptide Nucleic Acids," Science, 258:1481–1485, 1992.

Harriman et al., "Metallotexaphyrins: A New Family of Photosensitisers for Efficient Generation of Singlet Oxygen", J. Chem. Soc., Chem. Commun., 314–316, 1989.

Hendry and Sargeson, "Metal Ion Promoted Phosphate Ester Hydrolysis. Intramolecular Attack of Coordinated Hydroxide Ion," J. Am. Chem. Soc., 111:2521–2527, 1989.

Kim and Chin, "Dimethyl Phosphate Hydrolysis at Neutral pH," J. Am. Chem. Soc., 114:9792–9795, 1992.

Knubel et al., "Biomimitic Synthesis of an Octavinylogous Porphyrin with an Aromatic [34] Annulene System", Angew. Chem., Int. Ed. Engl., 27:1170–1172, 1988.

Komiyama et al., "Unprecedentedly Fast Hydrolysis of the RNA Dinucleoside Monophosphates ApA and UpU by Rare Earth Metal Ions," J. Chem. Soc. Chem. Commun., 640–641, 1992.

Lauffer, "Paramagnetic Metal Complexes as Water Proton Relaxation Agents for NMR Imaging: Theory and Design", Chem. Rev. 87:901–927, 1987.

LeGoff et al., "Synthesis of a [1, 5, 1, 5,] Platyrin, a 26 π-Electron Tetrapyrrolic Annulene", J. Org. Chem. 52:710–711, 1987.

Marks et al., "Large Metal Ion-Centered Template Reactions. Chemical and Spectral Studies of the Superphthalocyanine Dioxocyclopentakis (1-iminoisoindolinato) uranium (VI) and Its Derivatives", J. Am. Chem. Soc., 100:1695–1705, 1978.

Menger et al., "Phosphate Ester Hydrolysis Catalyzed by Metallomicelles," J. Am. Chem. Soc., 109:2800–2803, 1987.

Modak et al., "Toward Cheimcal Ribonucleases. 2. Synthesis and Characterization of Nucleoside-Bipyridine Conjugates. Hydrolytic Cleavage of RNA by Their Copper(II) Complexes," J. Am. Chem. Soc., 113:283–291, 1991.

Morrow et al., "Efficient Catalytic Cleavage of RNA by Lanthanide (III) Macrocyclic Complexes: Toward Synthetic Nucleases for in Vivo Applications," J. Am. Chem. Soc., 114:1903–1905, 1992.

Phillips and Wasserman, "Promise of Radiosensitizers and Radioprotectors in the Treatment of Human Cancer," *Cancer Treatment Reports*, 68(1):291–301, 1984.

Ranganathan et al., "Design of a Chemical Nuclease Model with (Lys)$_2$Cu as the Core Motif," *Journal of the Chemical Society*, 4:337–339, 1993.

Rexhausen et al., "The Synthesis of a New 22 π-Electron Macrocycle: Pentaphyrin", J. Chem. Soc., Chem. Commun., 275, 1983.

Sessler, Jonathan L., "Texas-Sized Molecule," Discovery, 13(1):44–49, 1993.

Sessler et al., "Photodynamic Inactivation of Enveloped Viruses Using Sapphyrin, α22 π-Electron Expanded Porphyrin: Possible Approaches to Prophylactic Blood Purification Protocols," *SPIE Photodynamic Therapy: Mechanisms II.* 1203:233–245, 1990.

Sessler et al., "The Coordination Chemistry of Planar Pentadentate Porphyrin-Like Ligands", Comm. Inorg. Chem., 7:333–350, 1988.

Sessler et al., "An Expanded Porphyrin: The Synthesis and Structure of a New Aromatic Pentadentate Ligand", J. Am. Chem. Soc., 110:5586–5588, 1988.

Sessler et al., "A Water-Stable Gadolinium (III) Complex Derived from a New Pentadentate Expanded Porphyrin Ligand", Inorg. Chem., 28:3390–3393, 1989.

Sessler et al., "Binding of Pyridine and Benzimidazole to a Cadmium Expanded Porphyrin: Solution and X-ray Structural Studies", Inorg. Chem., 28:1333–1341, 1989.

Sessler et al., "Expanded Porphyrins: The Synthesis and Metal Binding Properties of Novel Tripyrrane–Containing Macrocycles", *J. Coord. Chem.*, 18:99–104, 1988.

Sessler et al., "A Water–Stable Gadolinium (III) Complex Derived from a New Pentadentate", *Chem. Absts.*, vol. 111:125716e (2 Oct. 1989) p. 720.

Sessler et al., "The Synthesis and Structure of a Novel 22 π–Electron Aromatic Pentadentate Macrocyclic Ligand: An Expanded Porphyrin", Toronto ACS Meeting, Jun. 1988.

Sessler et al., "'Texaphyrin': A Novel 22 π–Electron Aromatic Pentadentate Macrocyclic Ligand", ACS meeting, Los Angeles, Sep. 1988.

Sessler et al., "Tripyrroledimethine–derived (Texaphyrin–type) Macrocycles: Potential Photosensitizers Which Absorb in the Far–red Spectral Region", *SPIE*, Optical Methods for Tumor Treatment and Early Diagnosis: Mechanism and Technique, 1426:318–329, 1991.

Sessler et al., "Preparation of Lanthanide (III) Texaphyrin Complexes and Their Applications to Magnetic Resonance Imaging and Photodynamic Therapy, " *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Sessler et al., "Synthesis and Structural Characterization of Lanthanide (III) Texaphyrins," *Inorganic Chemistry*, 32(14):3175–3187, 1993.

Sessler et al., "Synthesis and Crystal Structure of a Novel Tripyrrane–Containing Porphyrinogen–Like Macrocycle," *J. Org. Chem.*, 52:4394–4397, 1987.

Sessler and Burrell, "Extended Porphyrins," *Topics in Current Chemistry*, 161:180–273, 1991.

Shelton and Morrow, "Catalytic Transesterification and Hydrolysis of RNA by Zinc (II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Stinson, "Unusual Porphyrin Analog Promises Many Applications, " *Chemical and Engineering News*, 26–27, Aug. 8, 1988.

Sumaoka et al., "Remarkably Fast Hydrolysis of 3', 5', –=Cyclic Adenosine Monophosphate by Cerium (III) Hydroxide Cluster," *J. Chem. Soc. Chem. Comm.*, 2 pp., 1992.

"Tentative Rules for Carbohydrate Nomenclature Part 1 (1969)," *Handbook of Biochemistry and Molecular Biology*, 3rd ed., Fasman, Ed., CRC Press, Cleveland, Ohio.

To and Neiman, "The Potential For Effective Antisense Inhibition of Retroviral Replication Mediated by Retroviral Vectors," *Gene Regulation: Biology of Antisense RNA and DNA*, 261–271, 1992.

Tweedle et al., "Principles of Contrast–Enhanced MRI", in Magnetic Resonance Imaging, 2nd ed. Partain, et al, Eds., W. B. Saunders: Philadelphia, I:793–809, 1988.

Vogel et al., "Porphycene—a Novel Porphin Isomer", *Angew. Chem., Int. Ed. Engl.*, 25:257–259, 1986.

Vogel et al., "2, 7, 12, 17 –Tetrapropylporphycene—Counterpart of Octaethylporphyrin in the Porphycene Series", *Angew. Chem., Int. Ed. Engl.*, 26:928–931, 1987.

Wagener and Beyrich, "Radiosensitizer–Biochemie und Tumortherapeutische Erfahrungen," *Pharmazie*, 47:815–824, 1992.

"Äthylamino–2–methyl–propanol–(1)," *Beilstein's Handbuch*, 4:785, 1950.

Dialog Search Report dated Jun. 9, 1993.

Dialog Search Report dated Aug. 3, 1993.

Mody, T. D., et al., "Lutetium (III) Texaphyrin: A Novel Photodynamic Therapy Agent", abstract, 22nd Annual American Society for Photobiology, Scottsdale, AR, Jun. 25–29, 1994.

TEXAPHYRIN METAL COMPLEXES HAVING IMPROVED FUNCTIONALIZATION

The government may own certain rights in the present invention pursuant to National Institutes of Health grant AI28845.

This application is a continuation-in-part application of U.S. Ser. No. 08/135,118 filed Oct. 12, 1993, now U.S. Pat. No. 5,457,183, and a continuation-in-part of U.S. Ser. No. 08/098,514 filed Jul. 28, 1993. U.S. Ser. No. 08/135,118 is a continuation-in-part of 07/822,964 filed Jan. 21, 1992, since issued as U.S. Pat. No. 5,252,720, Oct. 12, 1993. U.S. Ser. No. 08/098,514 is a divisional application of U.S. Ser. No. 07/822,964 filed Jan. 21, 1992, since issued as U.S. Pat. 5,252,720 on Oct. 12, 1993. U.S. Ser. No. 07/822,964 was a continuation-in-part application of Ser. No. 07/771,393, filed Sep. 30, 1991, now abandoned, which was a continuation-in-part of Ser. No. 07/539,975, filed Jun. 18, 1990, since issued as U.S. Pat. No. 5,162,509 on Nov. 10, 1992 and a continuation of international application no. PCT/US90/01208, filed Mar. 6, 1990, now abandoned. U.S. Ser. No. 07/539,975 was a divisional application of U.S. Ser. No. 07/320,293, filed Mar. 6, 1989, since issued as U.S. Pat. No. 4,935,498, Jun. 19, 1990. All of the above-named patents and pending applications are incorporated by reference herein.

BACKGROUND OF THE INVENTION

Texaphyrin compounds are described in U.S. Pat. Nos. 4,935,498, 5,162,509, 5,252,720, 5,272,142 and 5,256,399, each of which is incorporated by reference herein. Texaphyrin refers to an "expanded porphyrin" pentadentate macrocyclic ligand. The compound is capable of existing in both its free-base form and of supporting the formation of a 1:1 complex with a variety of metal cations, such as $Cd^{2+}$, $Hg^{2+}$, $In^{3+}$, $Y^{3+}$, $Nd^{3+}$, $Eu^{3+}$, $Sm^{3+}$, $La^{3+}$, $Lu^{3+}$, $Gd^{3+}$, and other cations of the lanthanide series that are too large to be accommodated in a stable fashion within the 20% smaller tetradentate binding core of the well-studied porphyrins.

Large, or "expanded" porphyrin-like systems are of interest for several reasons: They could serve as aromatic analogues of the better studied porphyrins or serve as biomimetic models for these or other naturally occurring pyrrole-containing systems. In addition, large pyrrole containing systems offer possibilities as novel metal binding macrocycles. For instance, suitably designed systems could act as versatile ligands capable of binding larger metal cations and/or stabilizing higher coordination geometries than those routinely accommodated within the normally tetradentate ca.2.0Å radius porphyrin core. The resulting complexes could have important application in the area of heavy metal chelation therapy, serve as contrast agents for magnetic resonance imaging (MRI) applications, act as vehicles for radioimmunological labeling work, or serve as new systems for extending the range and scope of coordination chemistry.

A number of pentadentate polypyrrolic aromatic systems, including the "sapphyrins", "oxosapphyrins", "smaragdyrins", "platyrins" and "pentaphyrin" have been prepared and studied as their metal-free forms. A "superphthalocyanine" system is not capable of existence in either its free-base or other metal-containing forms. Thus, prior to the present inventors' studies, no versatile, structurally characterized, pentadentate aromatic ligands were available.

The water-soluble porphyrin derivatives, such as tetrakis(4-sulfonatophenyl)porphyrin (TPPS) cannot accommodate completely the large gadolinium(III) cation within the relatively small porphyrin binding core ($r \cong 2.0$Å), and, as a consequence, gadolinium porphyrin complexes are invariably hydrolytically unstable.

Photodynamic therapy (PDT) uses a photosensitizing dye, which localizes at, or near, a treatment site, and when irradiated in the presence of oxygen serves to produce cytotoxic materials, such as singlet oxygen ($O_2(^1\Delta_g)$), from benign precursors (e.g. ($O_2(^3\Sigma_g^-)$). While porphyrin derivatives have high triplet yields and long triplet lifetimes (and consequently transfer excitation energy efficiently to triplet oxygen), their absorption in the Q-band region parallels that of heme-containing tissues.

Hematoporphyrin derivative and Photofrin II® (oligomeric hematoporphyrin derivative) act as efficient photosensitizers for the photo-deactivation of cell-free HIV-1, herpes simplex (HSV), hepatitis and other enveloped viruses in far lower dosages than are required for tumor treatment. The success of this procedure derives from the fact that these dyes localize selectively at or near the morphologically characteristic, and physiologically essential, viral membrane ("envelope") and catalyze the formation of singlet oxygen upon photoirradiation. The singlet oxygen destroys the essential membrane envelope. This kills the virus and eliminates infectivity. Photodynamic blood purification procedures, therefore, rely on the use of photosensitizers which localize selectively at viral membranes.

In contrast to the literature of the porphyrins, and related tetrapyrrolic systems (e.g. phthalocyanines, chlorins, etc.), there are only a few reports of larger pyrrole-containing systems, and only a few of these meet the criterion of aromaticity deemed essential for long-wavelength absorption and singlet oxygen photosensitization. In addition to the present inventors' studies of texaphyrin, and "sapphyrin", first produced by Bauer et al. (1983) and Broadhurst et al. (1972) there appear to be only three large porphyrin-like systems which might have utility as photosensitizers. These are the "platyrins" of LeGoff et al. (1987), the stretched porphycenes of Vogel et al. (1990) and the vinylogous porphyrins of Gosmann et al. (1986). The porphycenes, (Vogel et al. 1986, Vogel et al. 1987), a novel class of "contracted porphyrins" also show promise as potential photosensitizers, (Aramendia et al. 1986).

The lowest energy Q-type band of the structurally characterized bispyridine cadmium(II) adduct of texaphyrin at 767 nm ($\epsilon$=51,900) in $CHCl_3$ is 10-fold more intense and red shifted by almost 200 nm as compared to that of a typical reference cadmium(II) porphyrin. Zinc(II) and cadmium(II) complexes of texaphyrin are effective photosensitizers for singlet oxygen, giving quantum yields for $^1O_2$ formation of between 60 and 70% when irradiated at 354 nm in air-saturated methanol, (Harriman et al. 1989). Related congeneric texaphyrin systems bearing substituents on the tripyrrole and/or phenyl portions and incorporating La(III) and/or Lu(III) metal centers have been found to produce $^1O_2$ in quantum yields exceeding 70% when irradiated under similar conditions. Thus, it is this remarkable combination of light absorbing and $^1O_2$ photo-sensitizing properties which makes these systems ideal candidates for use in photodynamic therapy and blood purification protocols.

The desirable properties of texaphyrins are:
1) appreciable solubility, particularly in aqueous media;
2) biolocalization in desired target tissue;
3) low intrinsic toxicity;
4) the ability to attach to solid matrices;
5) the ability to be attached to biomolecules;

6) efficient chelation of divalent and trivalent metal cations;

7) absorption of light in the physiologically important region of 690–880 nm;

8) high chemical stability;

9) ability to stabilize diamagnetic complexes that form long-lived triplet states in high yield and that act as efficient photosensitizers for the formation of singlet oxygen;

10) ability to chelate Gd(III) for magnetic resonance imaging;

11) a redox potential lower than that of oxygen for use as a radiosensitizer.

One of the disadvantages of the texaphyrin metal complexes of the parent patent applications is their short half-life. The $Y^{3+}$ and $In^{3+}$ complexes of texaphyrin have half-lives for decomplexation and/or ligand decomposition of about 3 weeks in 1:1 methanol-water mixtures. While such stability is adequate for some in vitro or in vivo applications, a greater degree of stability in aqueous solution is desirable. For example, a desired solution-phase shelf life of 2–3 years would facilitate the formulation of texaphyrin metal complexes as pharmaceutical products. The new molecules of the present invention address the problems of demetallation of the texaphyrin metal complex and the susceptibility of the imine bonds of the macrocycle to hydrolysis. The solution to these problems is expected to provide a texaphyrin which has a more desirable shelf life.

SUMMARY OF THE INVENTION

The present invention seeks to solve these problems by providing texaphyrin metal complexes having improved functionalization compared to those previously described. The improved functionalization is two-fold; firstly, addition of electron donating groups to positions 12, 15, 18 and/or 21 of the macrocycle contributes electrons to the aromatic $\pi$ system of the macrocycle which stabilizes the metal complex to demetallation and stabilizes the imine bonds to hydrolysis; and secondly, the addition of electron withdrawing groups to positions 15 or 18 renders the macrocycle more readily reduced, i.e. the redox potential will be lower and the macrocycle will more readily gain an electron to form a radical. The addition of substituents to the 12 and 21 positions of the macrocycle also offer steric protection for the imine bonds against possible in vivo enzyme hydrolysis. Thus, the macrocycles of the present invention represent molecules where an attempt has been made to optimize their structure and properties in terms of imine bond stabilization and low redox potential, properties that are expected to be important for radiosensitization as well as other applications.

Exemplary electron donating groups that may be employed in the practice of the invention include, among others, amino, alkylamino, hydroxyl, acylamino, alkoxy, acyloxy, alkyl, aryl, and alkenyl. Electron withdrawing groups include halide other than iodide, haloalkyl other than iodoalkyl, formyl, acyl, carboxylic acid, ester, acyl chloride, sulfonic acid, and nitro among others. Other potential electron donating or withdrawing groups will be apparent to one of skill in the art in light of the present disclosure.

In certain embodiments, the present invention provides a texaphyrin having the structure:

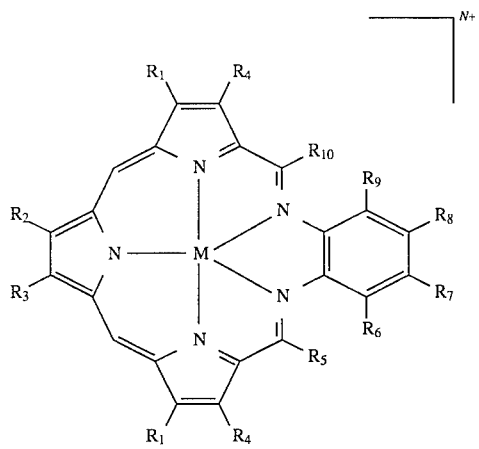

M may be H, a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2^{+2}$, or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$.

$R_1$–$R_4$ and $R_6$–$R_9$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

$R_5$ and $R_{10}$ are independently hydrogen, alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule. For this embodiment, at least one of $R_5$, $R_6$, $R_9$, and $R_{10}$ is other than hydrogen and N is an integer less than or equal to 2.

An aspect of the present invention is an embodiment where a substituent may be an electron donating group. In this case, $R_1$–$R_4$ and $R_6$–$R_9$ are independently hydrogen, hydroxyl, alkyl, aryl, hydroxyalkyl, oxyalkyl, oxyhydroxyalkyl, saccharide, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule.

In this embodiment, $R_5$ and $R_{10}$ are independently hydrogen, alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule. At least one of $R_5$, $R_6$, $R_9$, and $R_{10}$ is other than hydrogen and N is an integer less than or equal to 2.

In another embodiment of the present invention, $R_6$ or $R_9$ may have an electron withdrawing group. In that case, $R_1$–$R_4$, $R_7$ and $R_8$ are independently hydrogen, halide other than iodide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule. A couple may also be described as a linker, i.e. a reactive group for attaching another molecule at a distance from the texaphyrin macrocycle. An exemplary linker or couple is an amide, thiol, thioether or ether covalent bond as described in the examples for attachment of oligonucleotides and antibodies.

In this embodiment, $R_5$ and $R_{10}$ are independently hydrogen, alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule. $R_6$ and $R_9$ are independently halide other than iodide, formyl, acyl, carboxy, or nitro, at least one of $R_6$ and $R_9$ is other than hydrogen and N is an integer less than or equal to 2.

In the above-described texaphyrins, the halide other than iodide may be fluoride, chloride or bromide. The alkyl, aryl, hydroxyalkyl, oxyalkyl, oxyhydroxyalkyl, saccharide, carboxyalkyl, carboxyamidealkyl, oligonucleotide, antibody, hormone, peptide or sapphyrin molecule is covalently bonded to the texaphyrin via a carbon-carbon or a carbon-oxygen bond. The aryl may be a phenyl substituent or a phenyl having a nitro, carboxy, sulfonic acid, hydroxy, oxyalkyl or halide other than iodide substituent. In this case, the substituent on the phenyl group may be added in a synthetic step after the condensation step which forms the macrocycle.

Generally, water soluble texaphyrins retaining lipophilicity are preferred for the applications described herein. Water soluble means soluble in aqueous fluids to about 1 mM or better. Retaining lipophilicity means having greater affinity for lipid rich tissues or materials than surrounding nonlipid rich tissues or materials and in the case of viruses in suspension means affinity for the membranous coat of the virus. Lipid rich means having a greater amount of triglyceride, cholesterol, fatty acids or the like.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$.

The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to $2n+1$, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H((_{2m+1)-2w})O_wO_z$ or $N(R)\ OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

The carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than $((2n+1)-q)$, q is zero or a positive integer less than or equal to $2n+1$, $R^c$ is $(CH_2)_nCO_2R^d$, $(CH_2)_nCONHR^d$ or $(CH_2)_nCON(R^d)_2$ where n is a positive integer from 1 to 10; $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

For the above-described texaphyrins, the couple may be an amide, thiol, thioether or ether covalent bond, the oligonucleotide, the antibody, the hormone or the sapphyrin may have binding specificity for localization to a treatment site and the biological receptor may be localized to a treatment site.

A preferred embodiment of the present invention is a texaphyrin having a substituent on $R_5$ or $R_{10}$, then $R_6$ or $R_9$, respectively, is hydrogen, fluoride or hydroxyl. This embodiment includes texaphyrins having the structure:

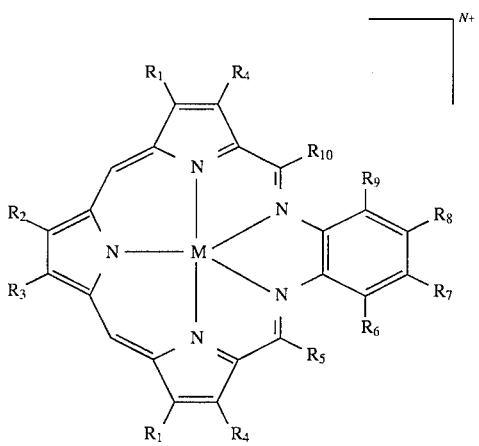

where $R_1$–$R_4$, $R_7$ and $R_8$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule; where at least one of $R_5$ and $R_{10}$ is alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule; and where $R_5$ is other than hydrogen, then $R_6$ is hydrogen, fluorine or hydroxyl; and where $R_{10}$ is other than hydrogen, then $R_9$ is hydrogen, fluorine or hydroxyl. N is an integer less than or equal to 2 and the metal cation is as described above.

A further preferred embodiment of the present invention is a texaphyrin having a substituent on $R_6$ or $R_9$, then $R_5$ or $R_{10}$, respectively, is hydrogen or methyl. This embodiment includes texaphyrins having the structure:

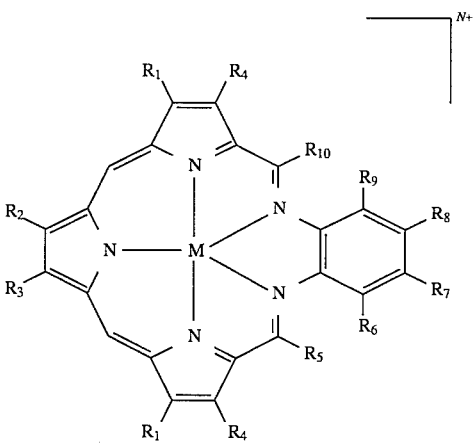

where $R_1$–$R_4$, $R_7$ and $R_8$ are as described above, at least one of $R_6$ and $R_9$ is halide other than iodide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, peptide having affinity for a biological receptor, a sapphyrin molecule, or a couple to an oligonucleotide, an antibody, a hormone, a peptide having affinity for a biological receptor or sapphyrin molecule; where $R_6$ is other than hydrogen, then $R_5$ is hydrogen or methyl; and where $R_9$ is other than hydrogen, then $R_{10}$ is hydrogen or methyl. N is an integer less than or equal to 2, and M is as described above.

More particularly preferred embodiments of the present invention are where $R_2$ and $R_3$ are $CH_2CH_3$ and $R_4$ is $CH_3$, where $R_5$ and $R_{10}$ are methyl, or where $R_5$ and $R_{10}$ are $(CH_2)_nCH_3$ where n is 0, 1, 2, 3 or 4. Furthermore, $R_5$ and $R_{10}$ may be phenyl having an $R_{11}$ substituent where $R_{11}$ is hydrogen, nitro, carboxy, sulfonic acid, hydroxy, oxyalkyl or halide other than iodide. In this case, the derivatization of the $R_{11}$ group may occur after the condensation of the macrocycle. Preferred substituents for $R_6$ include carboxy, alkyl or carboxyamidealkyl having a tertiary amide linkage. Preferred substituents for $R_7$, $R_8$ and $R_9$ are oxyalkyl.

An important embodiment of the present invention is a method for synthesizing a texaphyrin metal complex having a substituent at the 12, 15, 18 or 21 position. The method comprises the steps of: i) mixing, in an organic solvent, a nonaromatic texaphyrin having a substituent at the 12, 15, 18 or 21 position, a trivalent metal salt, a Bronsted base and an oxidant; and ii) allowing the mixture to react to form an aromatic texaphyrin metal complex having a substituent at the 12, 15, 18, or 21 position. A preferred means is to stir at ambient temperature or heat the mixture at reflux for at least two hours.

The nonaromatic texaphyrin having a substituent at the 12, 15, 18, or 21 position is conveniently produced by condensation of a tripyrrane aldehyde or ketone having structure A; and a substituted ortho-phenylenediamine having structure B:

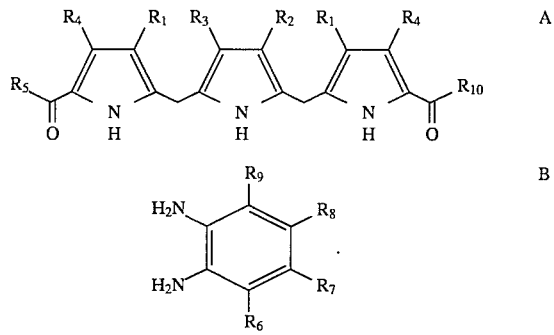

In this embodiment, $R_1$–$R_4$ and $R_6$–$R_9$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule.

$R_5$ and $R_{10}$ are independently hydrogen, alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule; and at least one of $R_5$, $R_6$, $R_9$, and $R_{10}$ is other than hydrogen.

In a preferred method of synthesis, the Bronsted base is triethylamine or N,N,N',N'-tetramethyl-1,8-diaminonaphthalene ("proton sponge") and the oxidant is air saturating the organic solvent, oxygen, platinum oxide, o-chloronyl or 2,3-dichloro-5,6-dicyano-1,4-benzoquinone. The stirring or heating at reflux step may comprise stirring or heating at reflux the mixture for at least 24 hours and the organic solvent may comprise methanol and chloroform, or methanol and benzene, or methanol and dimethylformamide. The trivalent metal salt may contain a cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^3$, $Tm^{+3}$, $Yb^{+3}$, $Lu^{+3}$, $La^{+3}$, and $U^{+3}$.

It is contemplated that the texaphyrins of the present invention will prove useful in a variety of applications. One example is in a method of deactivating a retrovirus or enveloped virus in an aqueous fluid. Such a method comprises the step of adding a texaphyrin metal complex having a substituent at the 12, 15, 18 or 21 position to said aqueous fluid and exposing the mixture to light to effect the formation of singlet oxygen. The aqueous fluid may be a biological fluid, blood, plasma, edema tissue fluid, ex vivo fluid for injection into body cavities, cell culture media, or a supernatant solution from cell culture and the like.

In blood, an exemplary viral deactivating method would include: i) mixing with blood in vitro or ex vivo a texaphyrin metal complex having a substituent at the 12, 15, 18 or 21 position capable of producing singlet oxygen when irradiated in the presence of oxygen; and ii) photoirradiating the mixture in vitro or ex vivo to produce singlet oxygen in a quantity cytotoxic to said retrovirus or enveloped virus. Exemplary retroviruses or enveloped viruses include herpes simplex virus I, cytomegalovirus, measles virus, or human immunodeficiency virus HIV-1. However, it is contemplated that the utility of the invention is not limited to these viruses. Preferred metal cations are diamagnetic metal cations and a preferred metal complex is the Lu(III), La(III) or In(III) complex of said texaphyrin.

A further application of the present invention is a method of light-induced singlet oxygen production comprising subjecting a texaphyrin metal complex having a substituent at the 12, 15, 18 or 21 position to light in the presence of oxygen. A method of photosensitization comprising the production of light-induced singlet oxygen using a texaphyrin metal complex having a substituent at the 12, 15, 18 or 21 position and an absorption range from about 730 to about 770 nanometers to form long-lived triplet states in high yield is another embodiment of the present invention. A texaphyrin metal complex having a substituent at the 12, 15, 18 or 21 position has the structure as described previously in this summary section, however, for these applications, M is a diamagnetic metal cation, for example, In(III), Zn(II), Cd(II), Lu(III) or La(III). Intrinsic biolocalization selectivity means having an inherently greater affinity for certain tissues relative to surrounding tissues.

Further aspects of the present invention include the use of a texaphyrin paramagnetic-metal complex having a substituent at the 12, 15, 18 or 21 position in the following methods which take advantage of the high relaxivity of these compounds: i) a method of enhancement of relaxivity comprising the administration of said texaphyrin; ii) a method of magnetic resonance image enhancement comprising administering to a subject an effective amount of said texaphyrin; iii) a method of detection of neoplastic tissue in a patient comprising the steps of administering to a patient said texaphyrin in an amount effective to enhance a magnetic resonance image and detecting neoplastic tissue by magnetic resonance imaging of said patient; iv) a method of imaging an organ in a patient comprising administering to a patient said texaphyrin in an amount effective to enhance a magnetic resonance image of the organ and detecting the organ by magnetic resonance imaging of said patient (the organ may be liver, kidney or the upper GI tract); v) a method of imaging atheroma in a patient comprising administering to a patient said texaphyrin in an amount effective to enhance a magnetic resonance image of atheroma and detecting atheroma by magnetic resonance imaging of said patient.

For use in these imaging applications, the texaphyrin paramagnetic-metal complex has the structure as described in this summary section, however, M is a paramagnetic metal cation, such as a trivalent lanthanide metal other than Ln(III), Lu(III) and Pm(III). In particular, M may be Mn(II), Mn(III), Fe(III) or Gd(III) and is preferably Gd(III).

A method of treating a host harboring atheroma or benign or malignant tumor cells is also an aspect of the invention. An exemplary preferred method includes administering to the host as a first agent a texaphyrin detectable-metal complex having a substituent at the 12, 15, 18 or 21 position, said complex exhibiting selective biolocalization in such atheroma or tumor cells relative to surrounding tissue; determining localization sites in the host by reference to such detectable metal; administering to the host as a second agent a texaphyrin detectable-metal complex having a substituent at the 12, 15, 18 or 21 position and having essentially identical biolocalization property and exhibiting the ability to generate singlet oxygen upon exposure to light; and photoirradiating the second agent in proximity to said atheroma or tumor cells.

In the above-described method, the first agent is further defined as being a texaphyrin paramagnetic-metal complex, the paramagnetic metal serving as the detectable metal. In this case, determination of localization sites occurs by magnetic resonance imaging; and the second agent is a texaphyrin diamagnetic-metal complex. The paramagnetic metal is most preferably Gd(III) and the diamagnetic metal is most preferably La(III), Lu(III) or In(III). A variation of this method uses as a first agent a texaphyrin-gamma emitting metal complex that serves as a detectable metal, determination of localization sites occurs by gamma body scanning and the second agent is a texaphyrin-diamagnetic metal complex.

The texaphyrin has the structure described above where M is a detectable metal, preferably detectable by magnetic resonance imaging or by gamma scanning. Detectable as used herein means that the location may be found by localization means such as magnetic resonance imaging if the metal is paramagnetic or gamma ray detection if the metal is gamma emitting or using monochromatic X-ray photon sources. Selective biolocalization means having an inherently greater affinity for certain tissues relative to surrounding tissues. Essentially identical biolocalization property means the second agent is a texaphyrin derivative having about the same selective targeting characteristics in tissue as demonstrated by the first agent.

A method of treating a host harboring tumor cells comprises the steps of: i) administering to the host an effective amount of a texaphyrin diamagnetic-metal complex having a substituent at the 12, 15, 18 or 21 position, the complex exhibiting selective biolocalization in the tumor cells relative to surrounding tissue; and ii) photoirradiating the texaphyrin-diamagnetic metal complex in proximity to the tumor cells. The photoirradiating is generally at a wavelength of about 730 to 770 nanometers or may be from laser light. In these embodiments, the diamagnetic metal will typically be In(III), La(III) or Lu(III).

The present invention provides a method of radiation therapy for a host harboring a tumor. The method includes the steps of administering to the host a texaphyrin having a substituent in the 12, 15, 18 and/or 21 position(s), and administering ionizing radiation to the host in proximity to the tumor. The texaphyrin exhibits greater biolocalization in the tumor relative to non-tumor tissue and has radiosensitization properties. A tumor may be a benign or malignant tumor or may be atheroma. A texaphyrin having radiosensitization properties enhances cytotoxicity from ionizing radiation as compared to control experiments without the texaphyrin. Ionizing radiation includes but is not limited to x-rays, and internal and external gamma emitting radioisotopes.

An improved method of treating a host harboring a tumor comprises the further step of determining localization sites in the host by monitoring texaphyrin concentrations. The texaphyrin may be complexed with a metal, however, a metal is not necessary for radiosensitization. The metal is important to the stability of the texaphyrin complex. Monitoring texaphyrin concentrations means measuring fluorescence of an administered free base texaphyrin or by reference to the metal of an administered texaphyrin metal complex. If the metal is paramagnetic, then magnetic resonance imaging is used for measurement, if the metal is a gamma emitting radioactive metal, then γ emission is used for measurement.

A further improved method of treating a host harboring a tumor comprises the additional steps of administering to the host as a second agent a texaphyrin-diamagnetic metal complex having a substituent at the 12, 15, 18 or 21 position and having essentially identical biolocalization property and administering ionizing radiation and photoirradiation in proximity to the tumor.

Determining localization sites occurs by observing fluorescence from the texaphyrin. The metal is a gamma-emitting metal and determining localization sites occurs by gamma body imaging or the metal is a paramagnetic metal and determining localization sites occurs by magnetic resonance imaging. The ionizing radiation may be from an external source or the metal is a radioactive metal and ionizing radiation is from the radioactive metal in combination with radiation from an external source. The second agent has essentially identical biolocalization property as the first agent and exhibits the ability to generate singlet oxygen upon exposure to light. The photodynamic effect may be derived from anaerobic electron transfer processes. A preferred diamagnetic metal texaphyrin complex is the Lu(III), La(III) or In(III) complex of a texaphyrin.

In these methods, determining localization sites may occur by observing fluorescence from the texaphyrin. When the first agent is complexed with a metal, the metal may be a gamma-emitting metal and determining localization sites would occur by gamma body imaging, or the metal may be a paramagnetic metal and determining localization sites would occur by magnetic resonance imaging. The ionizing radiation may be from an external source or the metal may be a radioactive metal. In that case, the ionizing radiation is from the radioactive metal in combination with radiation from an external source. Exhibiting greater biolocalization in the tumor relative to non-tumor tissue means having an inherently greater affinity for tumor tissue relative to non-tumor tissue. Essentially identical biolocalization property means the second agent is a texaphyrin derivative having about the same selective targeting characteristics in tissue as demonstrated by the first agent. The first agent and the second agent may be the same texaphyrin.

A preferred embodiment of the present invention is a method of radiation therapy for a host harboring a tumor comprising the steps of i) administering to the host a pharmaceutically effective amount of the Gd complex of a texaphyrin having a substituent at the 12, 15, 18 and/or 21 position(s); and ii) administering ionizing radiation to the host in proximity to the tumor.

Another aspect of this invention is a method of imaging atheroma in a host comprising the administration to the host as an agent a texaphyrin-detectable-metal complex having a substituent at the 12, 15, 18 and/or 21 position(s), said complex exhibiting selective biolocalization in such atheroma; and imaging the atheroma in the host by reference to such detectable metal. The agent is preferably a texaphyrin-detectable-metal complex having a substituent at the 12, 15, 18 and/or 21 position(s), a paramagnetic metal serving as said detectable metal; and imaging of the atheroma occurs by magnetic resonance imaging. The paramagnetic metal is preferably Gd(III). The agent is preferably the Gd complex of said texaphyrin.

One skilled in the art would recognize in light of the present disclosure that sapphyrin-conjugated texaphyrin metal complexes may be used in methods for generating singlet oxygen. Sapphyrins compounds are disclosed in patent applications Ser. Nos. 454,298 and 454,301 which are incorporated by reference herein.

Texaphyrin metal complexes having increased solution phase stability are expected to be more stable in vivo. Increased stability achieved via specific, designed modifications of the texaphyrin skeleton could give rise to products with modified biolocalization properties. Selective targeting would improve the efficacy and utility of texaphyrins as diagnostic or therapeutic agents for the range of applications discussed herein.

DETAILED DESCRIPTION OF THE PREFERRED EMBODIMENTS

Figure 5:
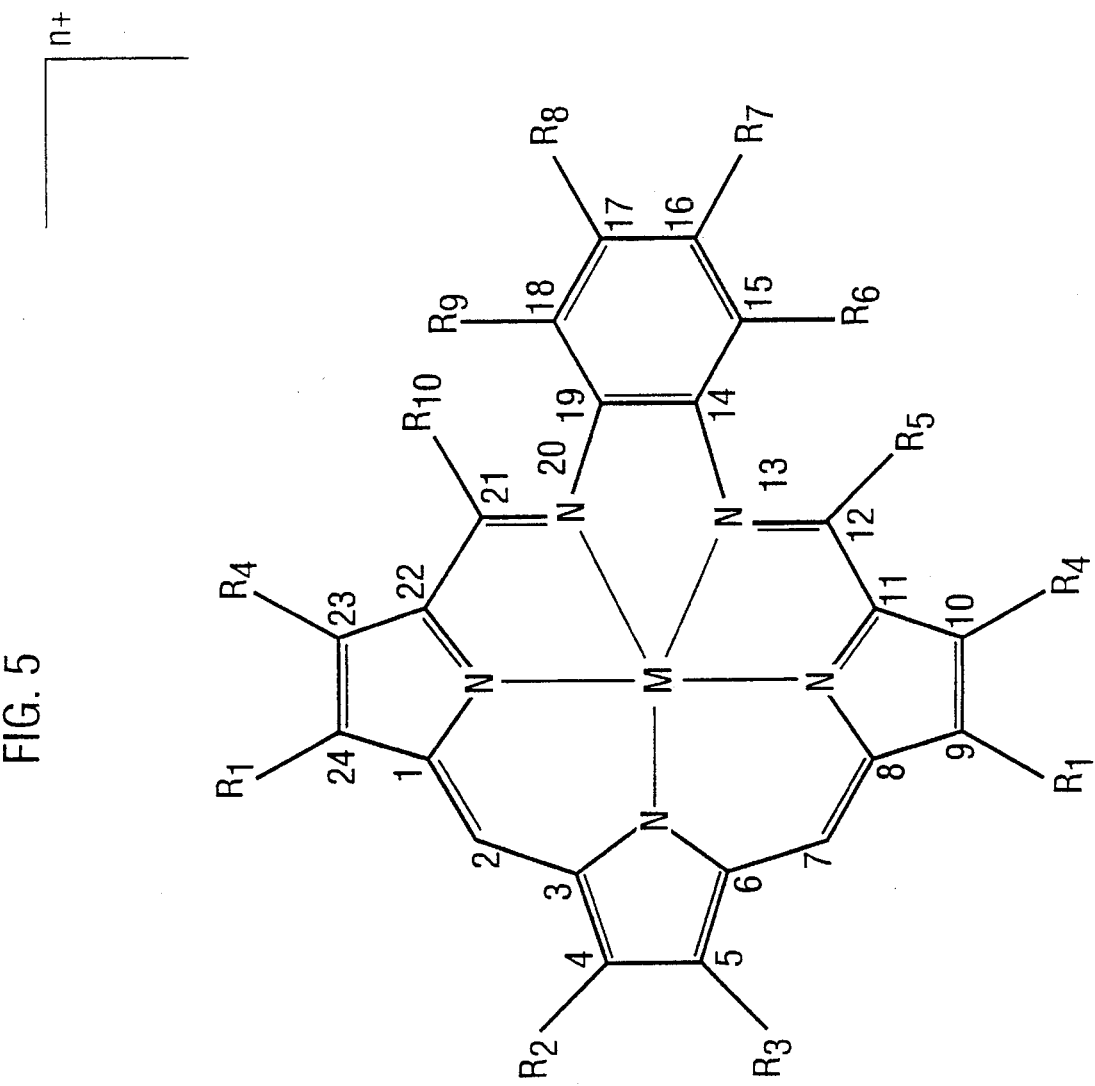
FIG. 5 shows a correlation of the IUPAC nomenclature for the positions of the atoms around the periphery of the macrocycle with the positions of the R groups of the present invention. $R_5$ is attached to position 12, $R_6$ is attached to position 15, $R_9$ is attached to position 18 and $R_{10}$ is attached to position 21.

The present invention involves metal complexes of texaphyrins having a substituent(s) at the 12, 15, 18 and/or 21 position(s) of the texaphyrin macrocycle and the synthesis and uses thereof. The nomenclature as used herein defines a substituent $R_5$ attached to position 12, $R_6$ attached to position 15, $R_9$ attached to position 18 and $R_{10}$ attached to position 21 of the macrocycle (FIG. 5).

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine.

Most preferred functionalizations are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Hydroxylated texaphyrins described in U.S. Pat. No. 5,252,720 and application Ser. No. 08/135,118 exhibit significant solubility in aqueous media, up to 1 mM or better, yet they retain affinity for lipid rich regions which allows them to be useful in a biological environment.

Electron donating substituents at the 12, 15, 18 and 21 positions of the macrocycle stabilize the molecule against decomposition processes involving hydrolysis of the imine bonds. Such substituents also stabilize the resulting complex against demetallation by contributing electrons to the aromatic π system. Such electron donating groups include hydroxyl, alkyl, haloalkyl other than iodoalkyl, aryl, hydroxyalkyl, oxyalkyl, oxyhydroxyalkyl, saccharide, carboxyalkyl, carboxyamidealkyl, an oligonucleotide, an antibody, a hormone, a peptide having affinity for a biological receptor, a sapphyrin molecule, or a couple to any of these molecules. Hydrolysis-resistant texaphyrin metal complexes are useful for localization, magnetic resonance imaging, radiosensitization, radiation therapy, fluorescence imaging, photodynamic tumor therapy and applications requiring singlet oxygen production for cytotoxicity.

Electron withdrawing substituents at the 15, 16, 17 and 18 positions of the macrocycle destabilize the aromatic π system and render the macrocycle more readily reduced, i.e. more easily able to gain an electron to form a radical. Such electron withdrawing groups include halide other than iodide, formyl, acyl, carboxy, or nitro substituents. Readily reducible texaphyrin metal complexes are useful for radiosensitization where the extent of radiation damage is dependent on the generation of hydroxyl and texaphyrin radicals.

The photophysical properties of various texaphyrin metal complexes are reported in U.S. Pat. 5,252,720 and include strong low energy optical absorptions in the 690–880 nm spectral range, a high triplet quantum yield and efficient production of singlet oxygen. Texaphyrin metal complexes of parent application Ser. No. 08/135,118, incorporated by reference herein, demonstrate enhanced cytotoxicity from radiation and enhanced nucleic acid strand scission in the presence of a gadolinium(III) metallotexaphyrin complex. U.S. Pat. No. 5,252,720 describes photosensitized inactivation of enveloped viruses and magnetic resonance imaging (MRI) of atheroma, liver, kidney and tumor using various substituted texaphyrin metal complexes. Altering the polarity and electrical charges of side groups of these macrocycles alters the degree, rate, and site(s) of binding to free enveloped viruses such as HIV-1 and to virally-infected peripheral mononuclear cells, thus modulating photosensitizer take-up and photosensitization of leukemia or lymphoma cells contaminating bone-marrow. Powerful techniques include the use of these texaphyrins in magnetic resonance imaging followed by photodynamic tumor therapy in the treatment of atheroma, and benign and malignant tumors or followed by sensitized X-ray treatment.

Examples 1–5 describe the synthesis of texaphyrin metal complexes having a substituent(s) at the 12, 15, 18 and/or 21 position(s) of the macrocycle. Examples 6–12 describe the use of texaphyrins of the present invention for imaging, radiosensitization, radiation therapy and photodynamic tumor therapy.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Synthesis of Compounds $1_C$, $1_E$, $1_F$ and $1_G$

Figure 1A:
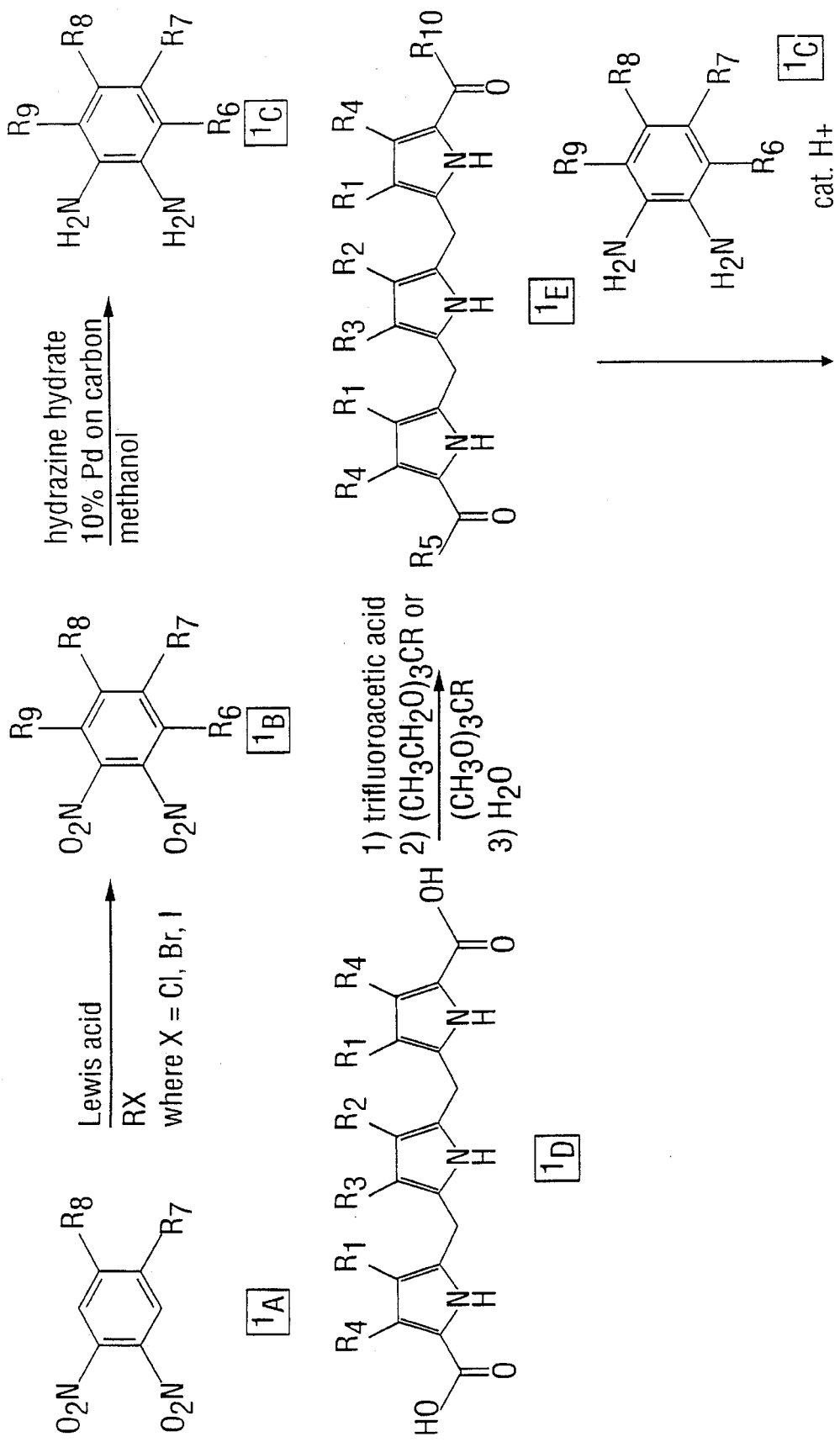
FIG. 1A and FIG. 1B summarize the synthesis of a texaphyrin metal complex having substituents at the 12($R_5$), 15($R_6$), 18($R_9$) and 21($R_{10}$) positions of the macrocycle (see FIG. 5 for definitions of positions). A tripyrrane ketone $1_E$ is condensed with a substituted ortho-phenylenediamine $1_C$ to yield the nonaromatic precursor $1_F$ which is complexed with a metal cation to form an aromatic texaphyrin metal complex $1_G$.
Figure 1B:
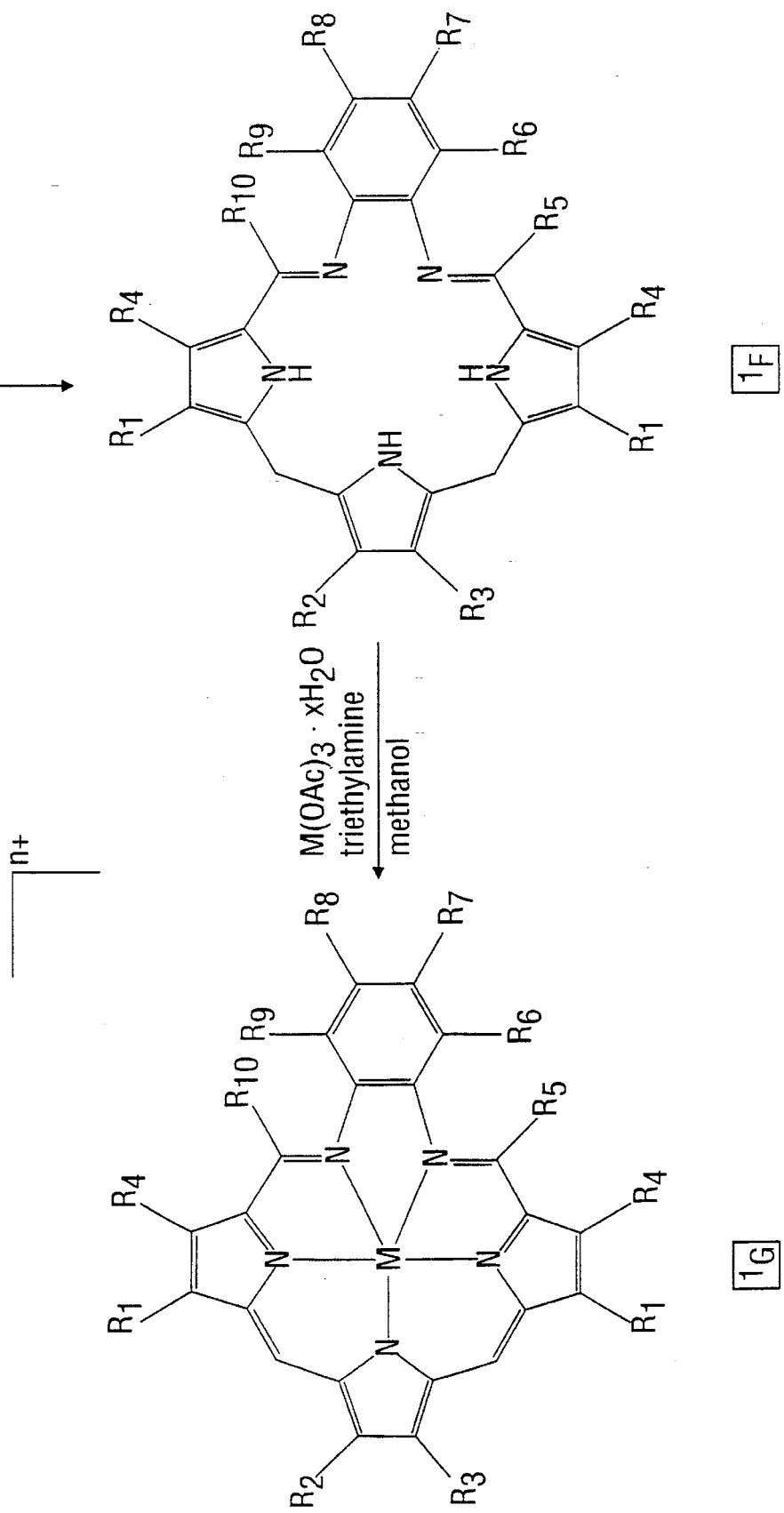

This example describes the synthesis of compounds depicted in FIG. 1A and FIG. 1B; a tripyrrane ketone $1_E$, a substituted ortho-phenylenediamine $1_C$, a nonaromatic texaphyrin $1_F$, and a metal complex of aromatic texaphyrin $1_G$.

All solvents and reagents are of reagent grade quality, available commercially, and are used without further purification. Sigma lipophilic Sephadex (LH-20-100) and Merck type 60 (230–400 mesh) silica gel are used for column chromatography.

$^1H$ and $^{13}C$ NMR spectra are obtained on a General Electric QE-300 (300 MHz.) spectrometer. Electronic spectra are recorded on a Beckman DU-7 spectrophotometer in $CHCl_3$. Infrared spectra are recorded, as KBr pellets, from 4000 to 600 $cm^{-1}$ on a Nicolet 510P FT-IR spectrophotometer. Chemical ionization mass spectrometric analyses (CI MS) are made using a Finnigan MAT 4023. Low resolution and high resolution fast atom bombardment mass spectrometry (FAB MS) are performed with a Finnigan-MAT TSQ-70 and VG ZAB-2E instruments, respectively. A nitrobenzyl alcohol (NBA) matrix is utilized with $CHCl_3$ as the co-solvent. Elemental analyses are performed by Atlantic Microlab, Inc. Melting points are measured on a Mel-temp apparatus and are uncorrected.

Tripyrrane ketone $1_E$: An example of the synthesis of a precursor to a tripyrrane ketone, the 2,5-bis[(3-(3-hydroxypropyl)-5-carboxyl-4-methylpyrrol-2-yl) methyl]-3,4-diethylpyrrole $6_E$, FIG. 6A and FIG. 6B, was presented in parent application, U.S. Ser. No. 08/135,118, incorporated by reference herein. In this example, $R_1$ is 3-hydroxypropyl, $R_2$ and $R_3$ are ethyl and $R_4$ is methyl. The tripyrrane portion of the molecule is important for linking the macrocycle to biologically important molecules such as an oligonucleotide, an antibody, a hormone, a peptide having affinity for a biological receptor, a sapphyrin molecule and the like.

The synthesis of compound $6_E$ provides teachings for the synthesis of $1_D$, precursor to tripyrrane ketone $1_E$ as follows.

2,5 -Bis [(5 -benzyloxycarbonyl-4-methyl-3 -methoxycarbonylethylpyrrol-2-yl)methyl]-3,4-diethylpyrrole. $6_C$, FIG. 6A. In a 500 mL round bottom flask was placed 250 mL of ethanol from an unopened bottle which is purged with dry nitrogen for ten minutes. 3,4-Diethylpyrrole $6_B$ (1.29 g, 0.01 mol) and 2-acetoxymethyl-5-benzyloxycarbonyl-4-methyl-3-methoxycarbonylethylpyrrole $6_A$ (7.83 g, 0.02 mol) were added and the mixture heated until all of the pyrroles dissolved. p-Toluenesulfonic acid (65 mg) was added and the reaction temperature maintained at 60° C. The reaction slowly changed color from a clear yellow to a dark red with the product precipitating out of the solution as the reaction progressed. After ten hours the reaction was cooled to room temperature, the volume reduced to one half on a rotary evaporator, and then placed in the freezer for several hours. The product was collected by filtration, washed with a small amount of cold ethanol to afford 4.61 g of an off-white fine powder (61%): $^1$H NMR (CDCl$_3$, 250 MHz): δ 1.14 (6H, t, CH$_2$CH$_3$), 2.23 (6H, s, pyrrole-CH$_3$), 2.31 (4H, t, CH$_2$CH$_2$CO$_2$CH$_3$), 2.50 (4H, q, CH$_2$CH$_3$), 2.64 (4H, t, CH$_2$CH$_2$CO$_2$CH$_3$), 3.60 (10H, br s, CH$_3$CO$_2$— and (pyrrole)$_2$-CH$_2$), 4.44 (4H, br s, C$_6$H$_5$CH$_2$), 6.99–7.02 (4H, m, aromatic), 7.22–7.26 (6H, m, aromatic) , 8.72 (1H, s, NH), 10.88 (2H, br s, NH); $^{13}$C NMR (CDCl$_3$, 250 MHz): δ 10.97, 16.78, 17.71, 19.40, 22.07, 35.09, 51.46, 65.32, 117.37, 119.34, 122.14, 126.58, 126.79, 127.36, 128.19, 133.55, 136.62, 162.35, 173.49; CI MS (M+H)$^+$ 750; HRMS 749.3676 (calc. for C$_{44}$H$_{51}$N$_3$O$_8$: 749.3676).

Figure 6A:
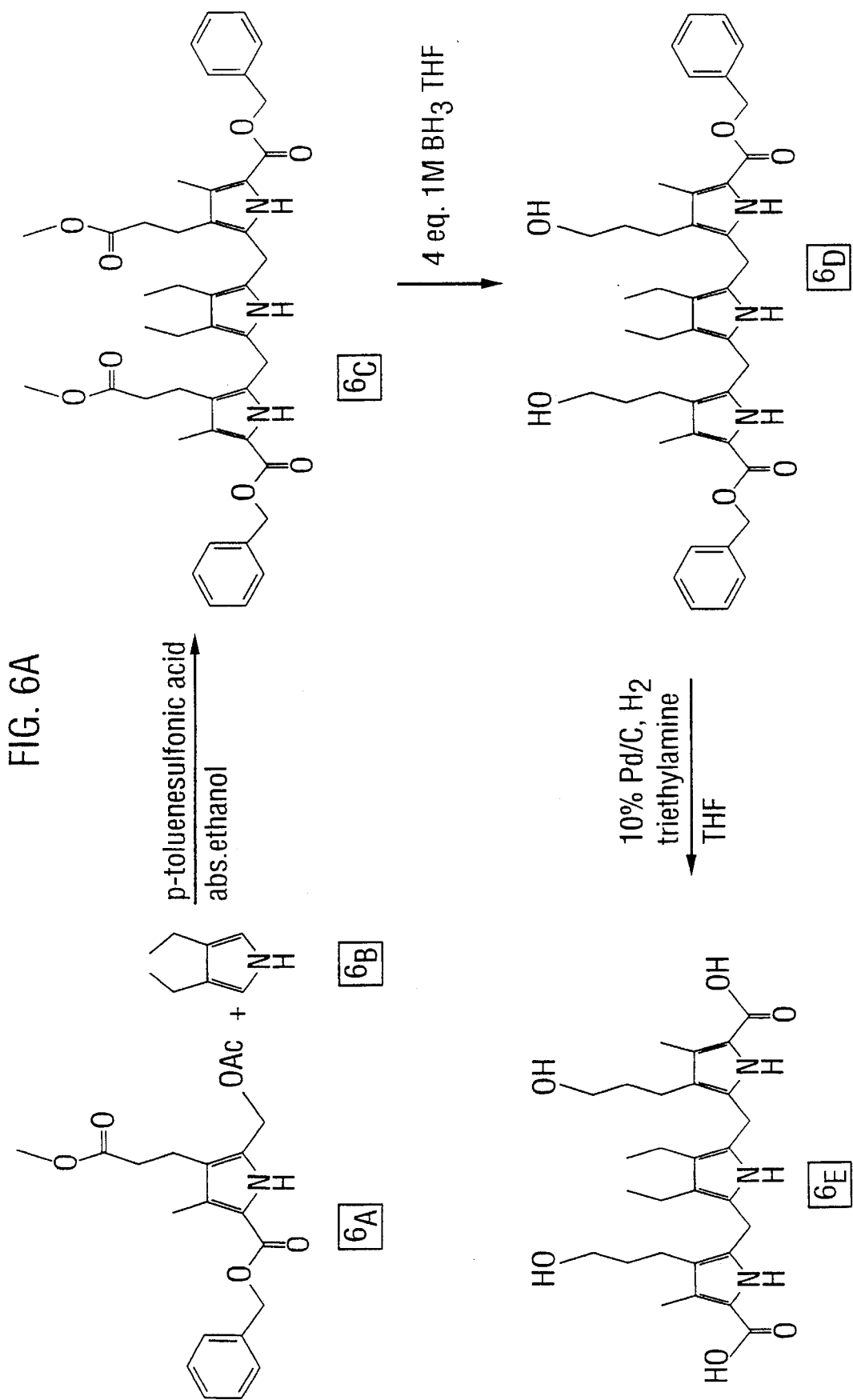
FIGS. 6A and FIG. 6B describe the synthesis of a precursor to a tripyrrane ketone, the 2,5-bis [(3-(3-hydroxypropyl)-5-carboxyl-4-methylpyrrol-2-yl) methyl]-3,4-diethylpyrrole $6_E$ (6A) and a synthetic scheme for attaching ester, carboxyl and tertiary amide groups at the $R_2$ and $R_3$ positions (6B).
Figure 6B:
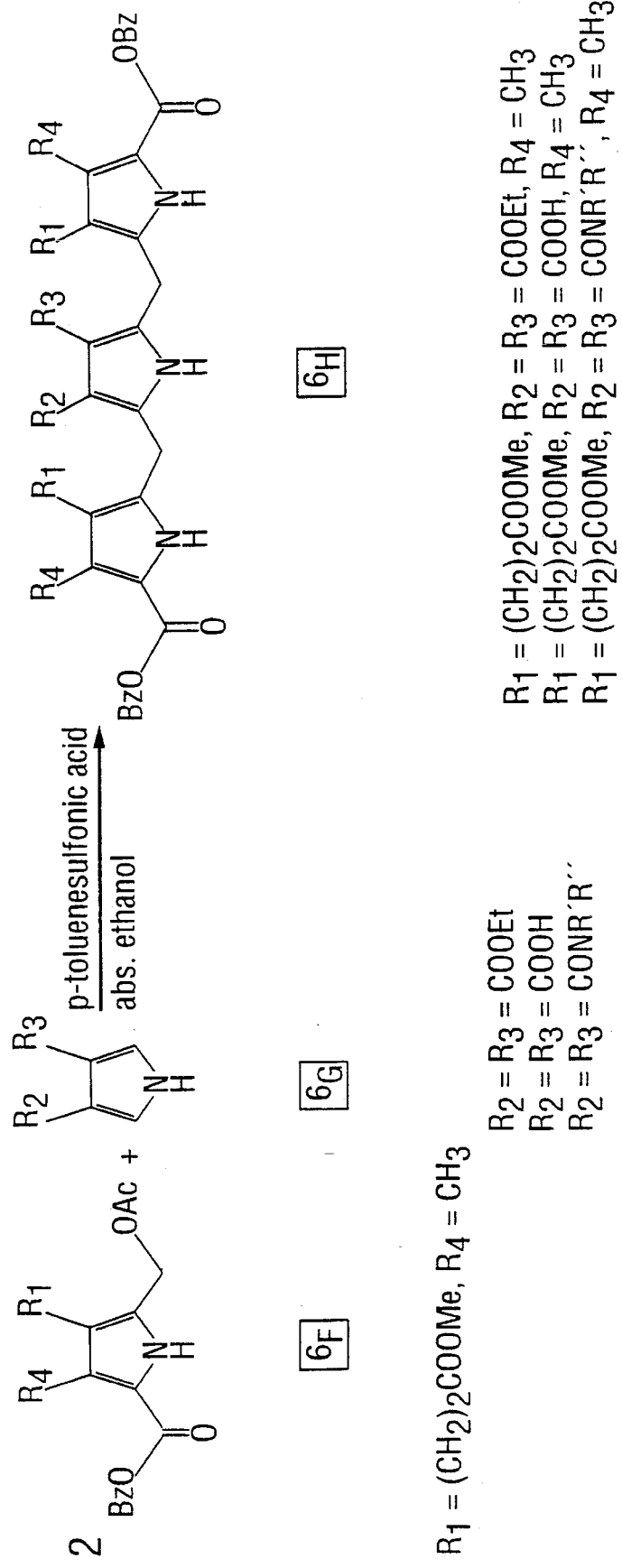

A synthetic scheme is presented in FIG. 6B for the attachment of an ester, a carboxyl and a tertiary amide as R$_2$ and R$_3$ substituents. The synthesis of compound $6_F$ is described in Kaesler et al. (1983).

2,5-Bis[(5-benzyloxycarbonyl-3-(3-hydroxypropyl)-4-methylpyrrol2yl)methyl]-3,4-diethylpyrrole. $6_D$, FIG. 6A. 2,5-Bis [(5-benzyloxycarbonyl-4-methyl-3-methoxycarbonylethylpyrrol- 2-yl)methyl]-3,4-diethylpyrrole $6_C$ (5.00 g, 0.007 mol) was placed in a three necked 100 mL round bottom flask and vacuum dried for at least 30 minutes. The flask was equipped with a thermometer, an addition funnel, a nitrogen inlet tube, and a magnetic stir bar. After the tripyrrane was partially dissolved into 10 mL of dry THF, 29 mL of borane (1M BH$_3$ in THF) was added dropwise with stirring. The reaction became mildly exothermic and was cooled with a cool water bath. The tripyrrane slowly dissolved to form a homogeneous orange solution which turned to a bright fluorescent orange color as the reaction went to completion. After stirring the reaction for one hour at room temperature, the reaction was quenched by adding methanol dropwise until the vigorous effervescence ceased. The solvents were removed under reduced pressure and the resulting white solid redissolved into CH$_2$Cl$_2$. The tripyrrane was washed three times with 0.5M HCl (200 mL total), dried over anhydrous K$_2$CO$_3$, filtered, and the CH$_2$Cl$_2$ removed under reduced pressure until crystals of the tripyrrane just started to form. Hexanes (50 mL) was added and the tripyrrane allowed to crystallize in the freezer for several hours. The product was filtered and again recrystallized from CH$_2$Cl$_2$/ethanol. The product was collected by filtration and vacuum dried to yield 3.69 g of an orangish white solid (76%): mp 172–173° C.; $^1$H NMR (CDCl$_3$, 300 MHz): δ 1.11 (6H, t, CH$_2$CH$_3$), 1.57 (4H, p, CH$_2$CH$_2$CH$_2$OH), 2.23 (6H, s, pyrrole-CH$_3$), 2.39–2.49 (8H, m, CH$_2$CH$_3$ and CH$_2$CH$_2$CH$_2$OH), 3.50 (4H, t, CH$_2$CH$_2$CH$_2$OH), 3.66 (4H, s, (pyrrole)$_2$-CH$_2$), 4.83 (4H, s, C$_6$H$_5$—C$_2$), 7.17–7.20 (4H, m, aromatic) , 7.25–7.30 (6H, m, aromatic), 8.64 (1H, s, NH), 9.92 (2H, s, NH); $^{13}$C NMR (CDCl$_3$, 300 MHz): δ 10.97, 16.72, 17.68, 20.00, 22.38, 33.22, 62.01, 65.43, 117.20, 119.75, 120.72, 122.24, 127.23, 127.62, 128.30, 132.95, 136.60, 162.13; FAB MS (M$^+$) 693.

2,5-Bis [(3-(3-hydroxypropyl)-5-carboxyl-4-methylpyrrol-2-yl) methyl]-3,4-diethylpyrrole $6_E$, FIG. 6A. 2,5-Bis [(3-(3-hydroxypropyl)-5-benzyloxycarbonyl-4 -methylpyrrol-2-yl)methyl]- 3,4-diethylpyrrole $6_D$ (15.0 g, 0.02 mol) was placed in a 1 L round bottom flask and dried in vacuo for ca. 30 min. The tripyrrane was dissolved in dry THF (600 mL) with triethylamine (10 drops) and 10% Pd on carbon (600 mg) and the reaction was stirred at room temperature under one atmosphere of H$_2$. After 15 h, the suspension was filtered through celite to remove the catalyst and the resulting clear solution was concentrated under reduced pressure to yield a light pink solid. This material, obtained in near quantitative yield, was taken on to the next step without further purification.

A carboxyl tripyrrane $1_D$ (a specific example presented as $6_E$ in FIG. 6A) (0.02 mol) is placed in a 250 mL round bottom flask and dried in vacuo for ca. 1 h. At room temperature under nitrogen, trifluoroacetic acid (31 mL, 0.40 mol) is added dropwise via syringe. The tripyrrane dissolves with visible evolution of CO$_2$ to form a homogeneous yellow solution. The reaction is stirred at room temperature for ca. 15 min, then cooled to 0° C. using a water/ice bath. A triethyl-ortho-ester (or trimethyl-ortho-ester, ca. 18 eq) is added to the reaction mixture dropwise with stirring after which the reaction is stirred for an additional 15 minutes at 0° C. If the ester is acetate, then a methyl group would be attached, propionate would attach an ethyl group, for example. The reaction is warmed to room temperature and 100 mL of water added dropwise. After stirring the resulting two phase mixture for ca. 30 minutes, the reaction mixture is extracted three times with CH$_2$Cl$_2$. The CH$_2$Cl$_2$ extracts are combined and washed three times with 1M aq. NaHCO$_3$ , once with water, dried over anhydrous sodium sulfate, filtered, and the solvent removed under reduced pressure. The resulting solid is recrystallized from CH$_2$Cl$_2$/hexanes.

Substituted ortho-phenylenediamine: The synthesis of an ortho-phenylenediamine substituted at the 4 and 5 positions is described in U.S. Pat. No. 5,252,720 and application Ser. No. 08/135,118.

Texaphyrin macrocycles having a free carboxyl or a free amino group for further derivatization on the benzene ring portion of the molecule may be synthesized by replacing ortho-phenylenediamine with 3,4 diaminobenzoic acid or 3,4 diaminoaniline. One skilled in the art of organic synthesis would realize in light of the present disclosure that other substituted 1,2-o-phenylenediamines may be used as a precursor, e.g., a 1-2-o-phenylenediamine that is differentially substituted in the 4 and 5 positions. This substitution may be the result of different functionalities being present or specific protection and standard organic and/or biochemical transformations having been carried out. Such macrocycles can be further functionalized to derivatives having an antibody, oligonucleotide, protein, peptide, sapphyrin and the like on one position of the B portion of the molecule.

Synthesis of $1_C$, FIG. 1A and FIG. 1B: Compound $1_A$ of FIG. 1A and FIG. 1B (a 1,2-dialkyl-4,5-dinitrobenzene) is reacted with an alkyl halide where the halide is chloride, bromide or iodide in the presence of a Lewis acid such as AlCl$_3$, for example. The 3 and 6 positions of the phenyl ring are derivatized with the alkyl group to form compound $1_B$. A mixture of reactants having a single halide and different alkyl groups may be used to generate different alkyl derivatives at the 3 and 6 positions. The yield of a particular product would be lower in this case.

A diamine $1_C$, (FIG. 1A and FIG. 1B) is obtained by reduction of the corresponding substituted dinitrobenzene ($1_B$, FIG. 1A and FIG. 1B) with hydrazine hydrate (1 mL) and 10% palladium on carbon (50 mg) in 40 mL refluxing absolute methanol. The resulting suspension may bubble for approximately 15–20 minutes and then turn colorless after 1 hour. At this point the reduction is complete as verified by TLC. The reaction solution is hot filtered through celite into a dry flask, covered with aluminum foil, and then concentrated to an oil. The diamine is taken to the next step without further purification. Ammonium formate in the presence of palladium (10% on carbon) catalyst may act as a mild, inexpensive and safe alternative to hydrazine hydrate in the above reaction and would be used, for example, when sensitive groups such as amide are present at other positions of the molecule.

Condensation of a tripyrrane ketone and a substituted ortho-phenylenediamine to form a nonaromatic texaphyrin having substituents at the 12, 15, 18 and/or 21 position(s): A tripyrrane ketone and a substituted ortho-phenylenediamine having substituents at the 3 and/or 6 position(s) are placed in a 2 L round bottom flask with 1000 mL of toluene and 200 mL of methanol. The solvents are purged with nitrogen prior to use. Concentrated HCl (0.5 mL) is added and the reaction heated to reflux under nitrogen. After 5 h the reaction is cooled to room temperature and the solvents removed under reduced pressure until the product precipitates out of solution. The remainder of the solvent is decanted off and the macrocycle is dried in vacuo. The product is recrystallized from methanol/diethylether and characterized by $^1$H NMR and $^{13}$C NMR.

Condensation of a diformyltripyrrole and a substituted ortho-phenylenediamine yields a nonaromatic texaphyrin having substituents in the 15, 16, 17 or 18 positions.

General procedure for the synthesis of lanthanide (III) complex of texaphyrin ($1_G$, FIG. 1A and FIG. 1B). One equivalent of the hydrochloride salt of the macrocycle, $1_F$, 1.5 equivalents of the Ln(OAc)$_3$.XH$_2$O metal salt, 2–3 equivalents of tetrabutylammonium nitrate (TBANO$_3$) and triethylamine (ca. 1 mL) are mixed together in methanol and heated to reflux under air. After completion of the reaction (as judged by the UV/vis spectrum of the reaction mixture), the solution is cooled to room temperature, the solvent is removed under reduced pressure and the crude complex dried in vacuo for several hours. A solution of dichloromethane/methanol (99:1 v/v) is added to the crude complex and the suspension is sonicated a few min. The suspension is filtered in order to remove impurities in the filtrate (incomplete oxidation products and excess triethylamine). The resulting solid is dissolved in methanol and then chloroform is added to reduce the polarity of the mixture (1:2 v/v). This solution is filtered through celite and loaded on a (pre-treated/pre-washed 1M NaNO$_3$) neutral alumina column (10 cm). The column is first eluted with a 1:10 (v/v) methanol/chloroform solution by gravity to remove any impurity. The metal complex is then obtained by eluting the column with chloroform containing increasing amounts of methanol (20–50%). The purified lanthanide(III) texaphyrin complex is recrystallized by dissolving the complex in methanol/chloroform and carefully layering the solution with a small amount of methanol, then with diethylether. The layered solution is kept at room temperature in the dark for a few days. The lanthanide(III) texaphyrin complex is recrystallized twice for analytically pure measurements and characterizations.

Lanthanum(III), Cerium(III), Praseodymium(III), Neodymium(III), Samarium(III), Europium(III), Gadolinium (III), Terbium(III), Dysprosium(III), Holmium(III), Erbium(III), Thulium(III), Ytterbium(III), Lutetium(III) complexes of texaphyrin: The hydrochloride salt of macrocycle $1_F$ (0.407 mmol), and one of the following lanthanide salts: La(OAc$_3$)$_3$.6H$_2$O (0.814 mmol), Ce(OAc$_3$)$_3$.6H$_2$O (0.611 mmol), Pr(OAc$_3$)$_3$.5H$_2$O (0.611 mmol), Nd(OAc$_3$)$_3$.6H$_2$O (0.611 mmol), Sm(OAc$_3$)$_3$.5H$_2$O (0.611 mmol), Eu(OAc$_3$)$_3$.5H$_2$O (0.65 mmol), Gd(OAc$_3$)$_3$.5H$_2$O (1.5 mmol), Tb(OAc$_3$)$_3$.6H$_2$O (0.611 mmol), Dy(OAc$_3$)$_3$.5H$_2$O (0.611 mmol), Ho(OAc$_3$)$_3$.5H$_2$O (0.611 mmol), Er(OAc$_3$)$_3$.5H$_2$O (0.611 mmol), Tm(OAc$_3$)$_3$.5H$_2$O (0.611 mmol), Yb(OAc$_3$)$_3$.5H$_2$O (0.611 mmol), or Lu(OAc$_3$)$_3$.H$_2$O (0.611 mmol), together with TBANO$_3$ (1.0 mmol) and triethylamine (ca. 0.5 mL) in 350 mL methanol are heated to reflux under air for 5–24 h. The workup uses the general procedure outlined above. The thulium and lutetium complexes may be more difficult to purify due to their lower solubility in methanol/chloroform solutions, which leads to a lower yield.

EXAMPLE 2

Synthesis of compounds $2_D$, $2_I$ and $3_E$

Figure 2A:
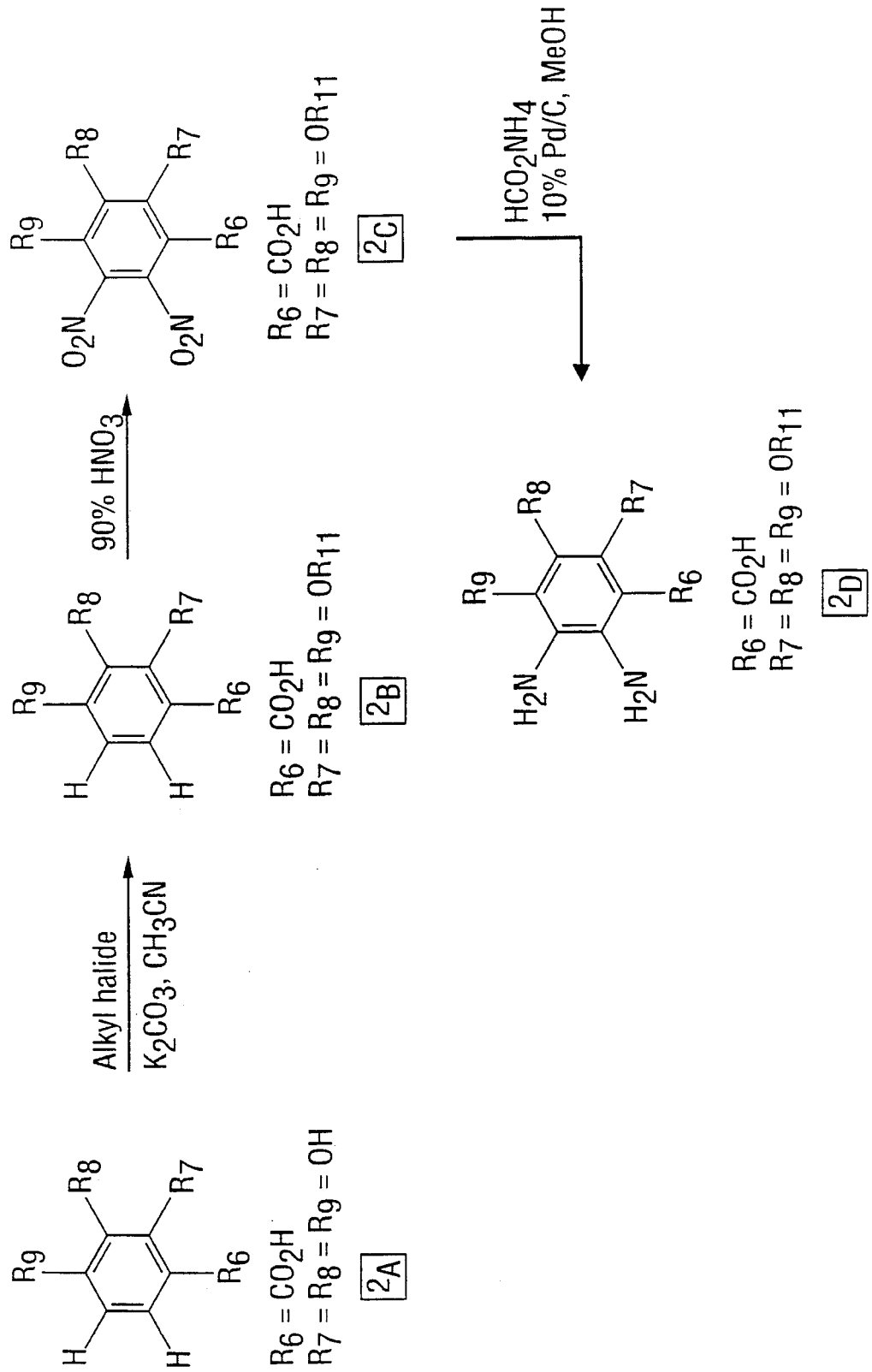
FIGS. 2A and FIG. 2B summarize the synthesis of substituted ortho-phenylenediamines for condensation with a tripyrrane ketone or a diformyltripyrrole to form texaphyrins having substituents at the 15, 16, 17 and 18 positions, in particular. The starting material in FIG. 2A is 2,3,4-trihydroxybenzoic acid and in FIG. 2B is 2,3,4-trihydroxybenzaldehyde.
Figure 2B:
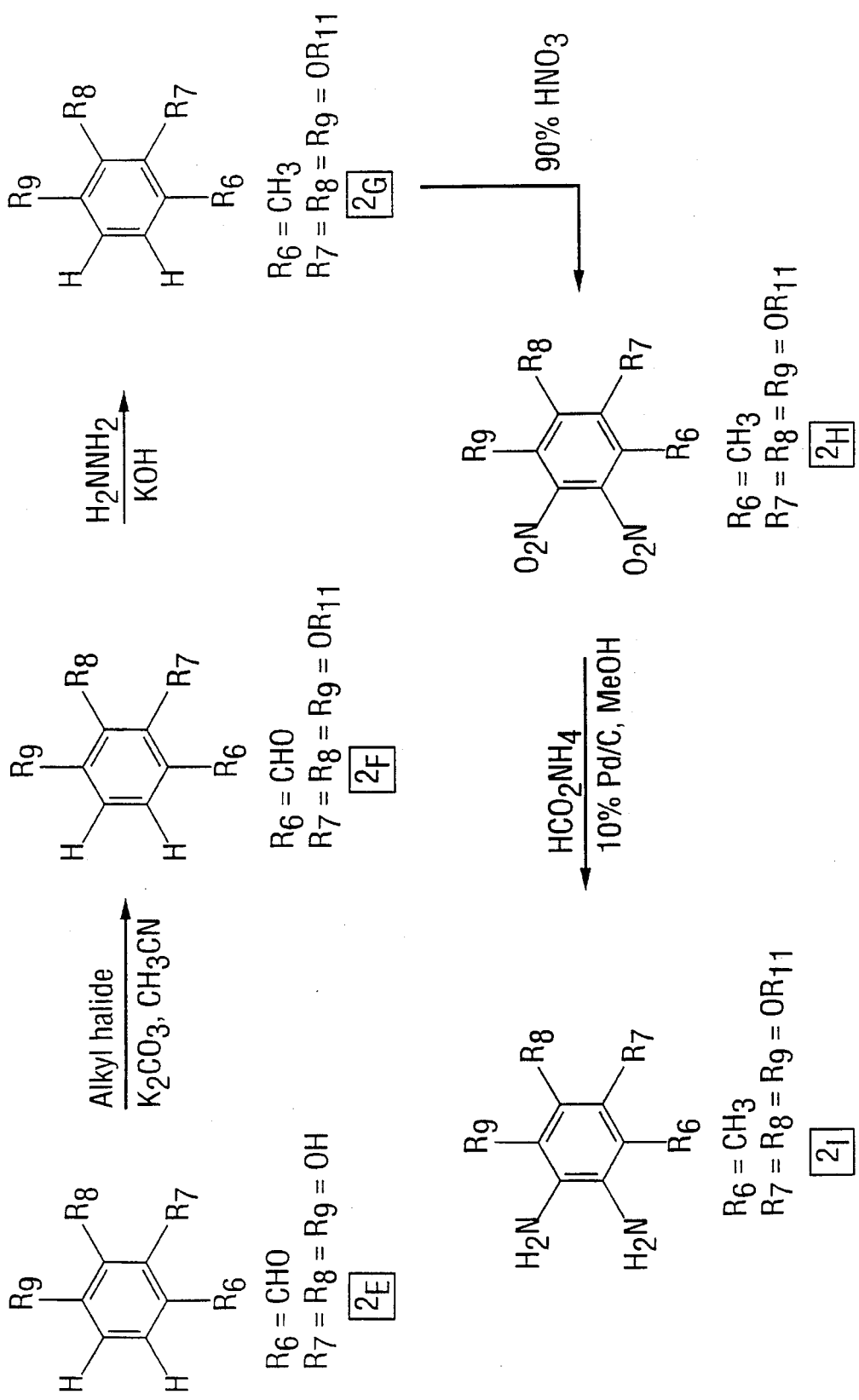

Ortho-phenylenediamine compounds having substituents bound to the phenyl ring via an oxygen are prepared as indicated in FIG. 2A and FIG. 2B. 2,3,4-Trihydroxybenzoic acid $2_A$, is reacted with an alkyl halide where the halide is chloride, bromide, or iodide in the presence of potassium carbonate and acetonitrile to form a trialkoxy derivative $2_B$. The alkyl group of the halide may be a primary or secondary alkyl having one or more hydroxy, alkoxy, carboxy, ester, amine, amide or protected amine substituents at positions at least one carbon removed from the site of halide attachment. These alkyl groups may be unsubstituted, singly or multiply functionalized. They may be branched or unbranched. Preferred alkyl groups are methyl, hydroxypropyl or methoxy-(ethoxy)$_n$ethoxy (a polyethylene glycol substituent). Compound $2_B$ is reacted with 90% nitric acid to form the dinitro derivative $2_C$ which is then reacted with either hydrazine hydrate or ammonium formate and 10% palladium on carbon in methanol to form compound $2_D$.

In a similar synthesis, starting with 2,3,4-trihydroxybenzaldehyde $2_E$ (FIG. 2B), reduction of the trialkoxy derivative $2_F$ with hydrazine in KOH results in a methyl derivative at the R$_6$ position to form 1,2,3-trialkoxy-4-methylbenzene $2_G$. The diamine is formed as depicted in 2A and described above.

Figure 3:
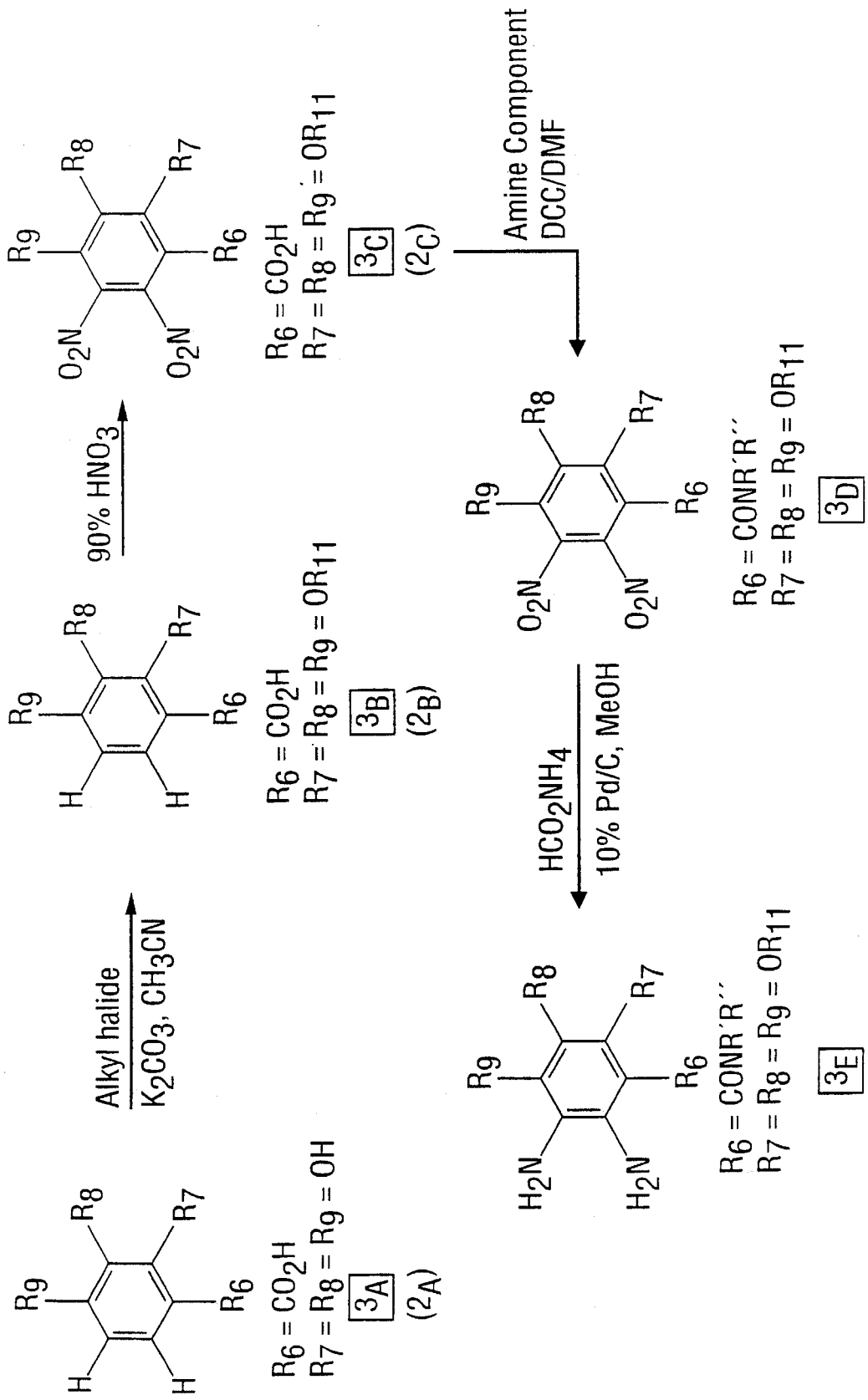
FIG. 3 summarizes the synthesis of a substituted ortho-phenylenediamine having a tertiary amide group at the $R_6$ position. The starting material is 2,3,4-trihydroxybenzoic acid.

FIG. 3 shows the formation of a tertiary amine at the R$_6$ position. Compound $3_C$ ($2_C$) is treated with an amine component in 1,3-dicyclohexylcarbodiimide and dimethylformamide to form $3_D$ having an amide linkage. Alternative coupling reagents include 1,1'-carbonyldiimidazole (CDI) or ECC. Reduction as described above yields the diamine for condensation with a tripyrrane ketone.

EXAMPLE 3

Synthesis of a T2B4 Texaphyrin

Figure 4A:
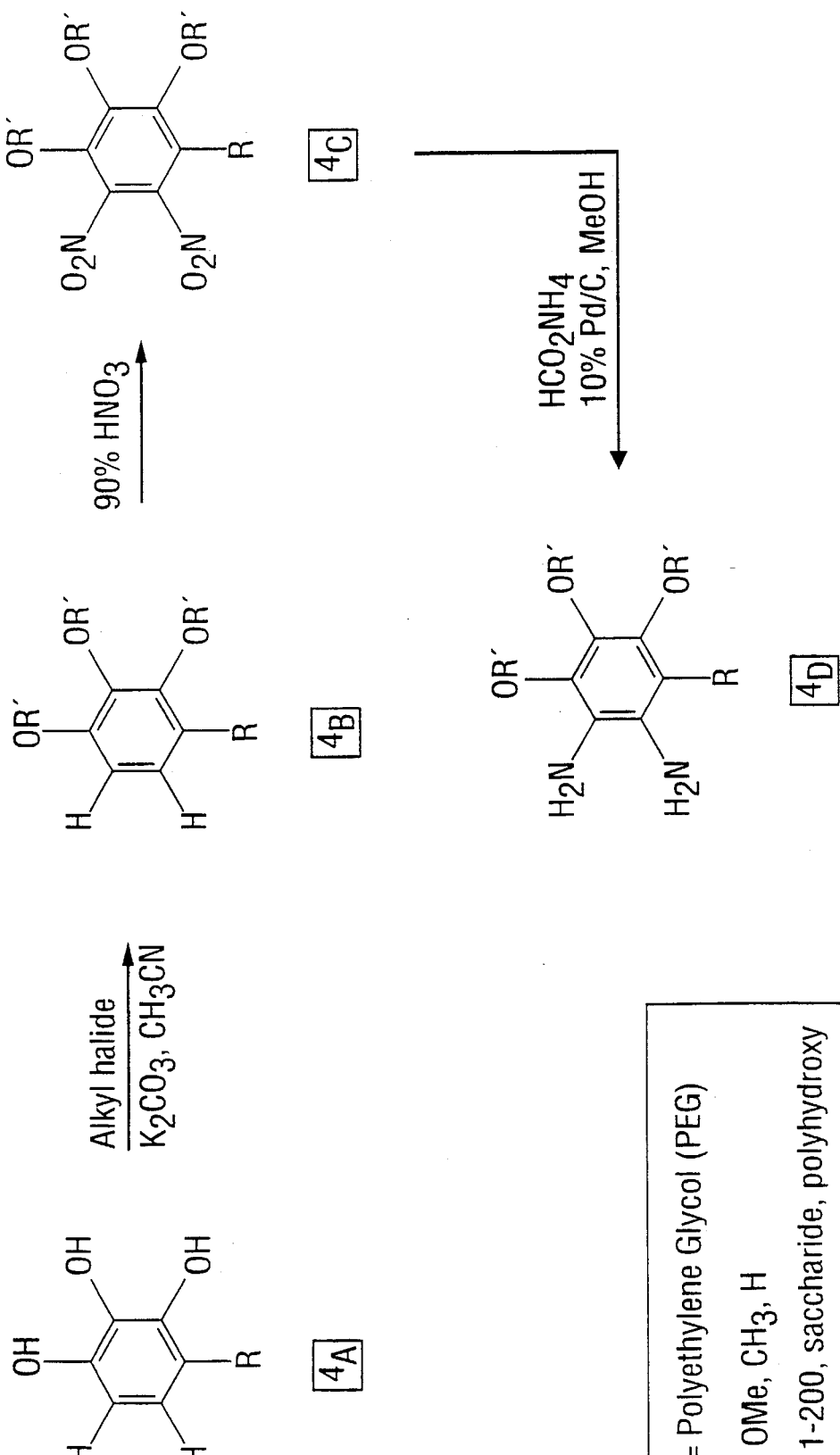
FIG. 4A and FIG. 4B show the synthesis of a lanthanide metal complex of a T2B4 texaphyrin. A diformyltripyrrole $4_E$ is condensed with a substituted ortho-phenylenediamine $4_D$ to form the nonaromatic precursor $4_F$.
Figure 4B:
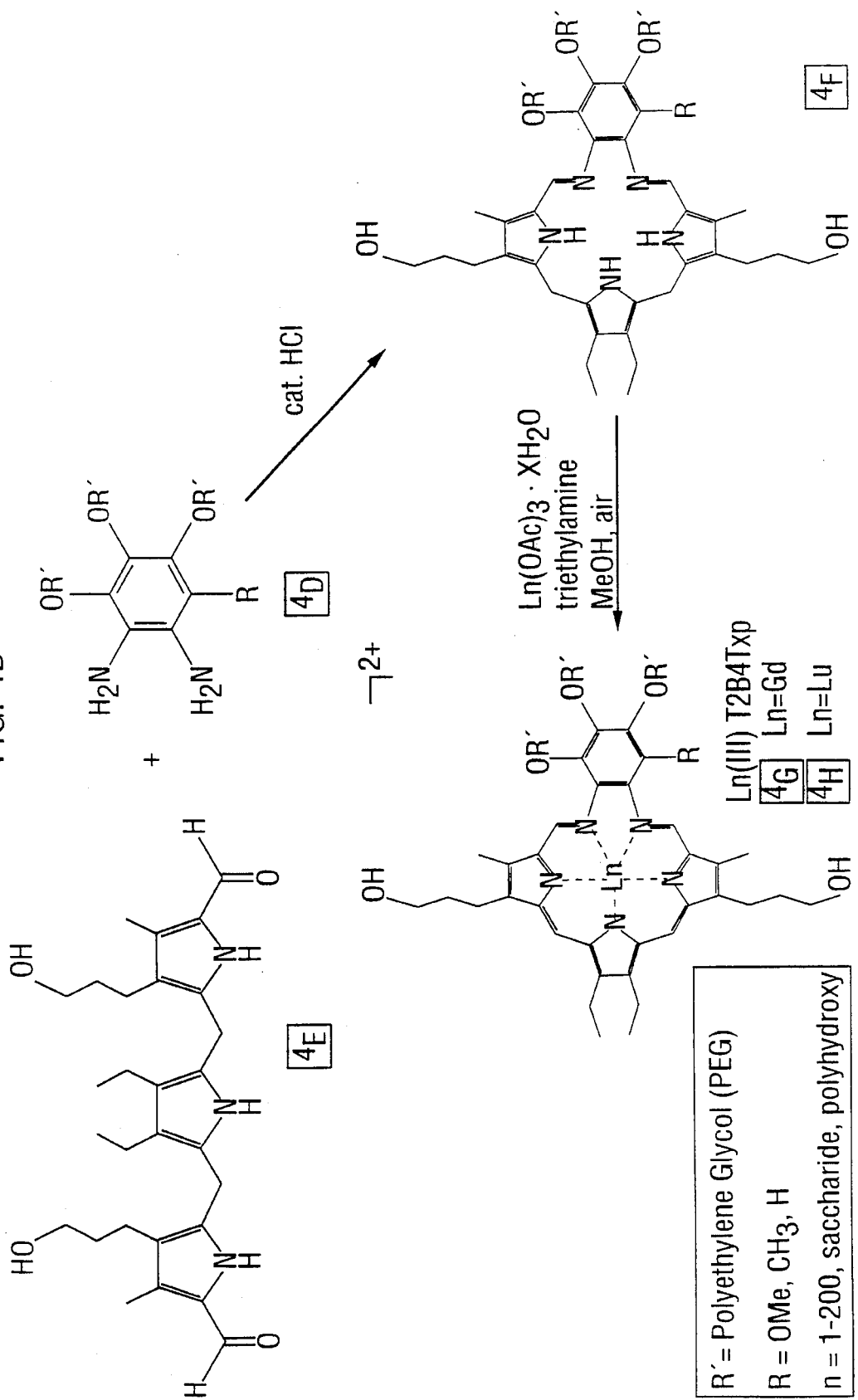

FIG. 4A and FIG. 4B show the synthesis of a lanthanide metal complex of a T2B4 texaphyrin. A diformyltripyrrole $4_E$ is condensed with a substituted ortho-phenylenediamine $4_D$ to form the nonaromatic precursor $4_F$. The synthesis of the substituted ortho-phenylenediamine $4_D$ was described in example 2 and the diformyltripyrrole was described in U.S. Pat. No. 5,252,720. In this example, R' may be polyethylene glycol (PEG) where the number of repeating ethoxy units may be as many as 200, a saccharide, a polyhydroxy substituent or the like. R may be methoxy, methyl or hydrogen.

EXAMPLE 4

$R_5$, $R_6$, $R_9$ and/or $R_{10}$ Substituents

R groups for texaphyrin macrocycles are described in U.S. Pat. No. 5,252,720 and application Ser. No. 08/135,118. Among others, groups on $R_6$ or $R_9$ may be: halide other than iodide, hydroxyl, alkyl, aryl, haloalkyl other than iodoalkyl, nitro, formyl, acyl, hydroxyalkyl, oxyalkyl, oxyhydroxyalkyl, saccharide, carboxy, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule.

Groups on $R_5$ or $R_{10}$ may be alkyl, aryl, hydroxyalkyl, oxyalkyl, oxyhydroxyalkyl, carboxyalkyl, carboxyamidealkyl or a couple to a saccharide, an oligonucleotide, an antibody, a hormone, a peptide having affinity for a biological receptor or a sapphyrin molecule, for example.

Electron donating substituents may be hydroxyl, alkyl, aryl, hydroxyalkyl, oxyalkyl, oxyhydroxyalkyl, saccharide, carboxyalkyl, carboxyamidealkyl, an oligonucleotide, an antibody, a hormone, a peptide having affinity for a biological receptor, a sapphyrin molecule, or a couple to an oligonucleotide, an antibody, a hormone, a peptide having affinity for a biological receptor or a sapphyrin molecule.

Figure 7A:
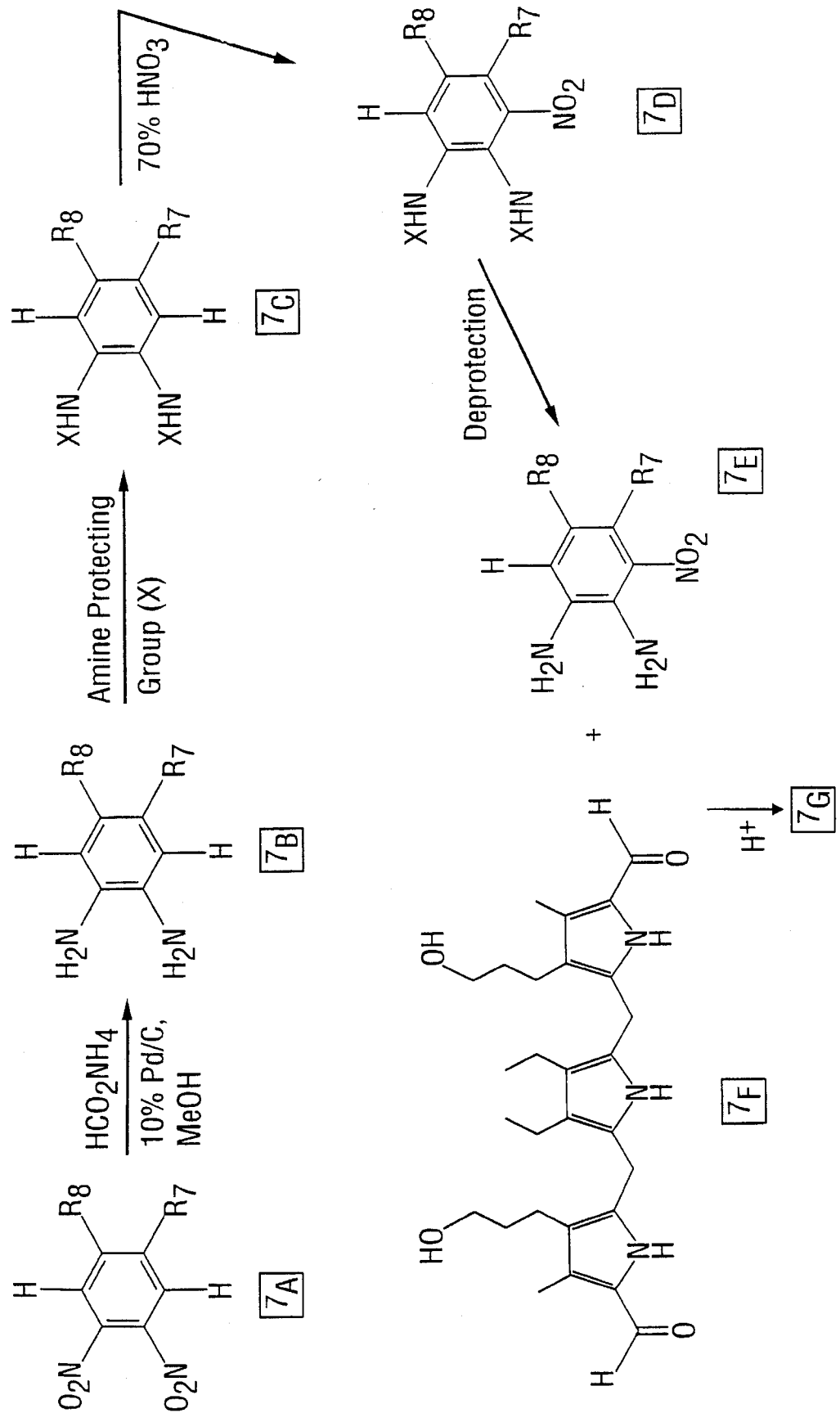
FIG. 7A and FIG. 7B show a synthetic scheme for attaching a nitro group at the $R_2$ or $R_9$ position.
Figure 7B:
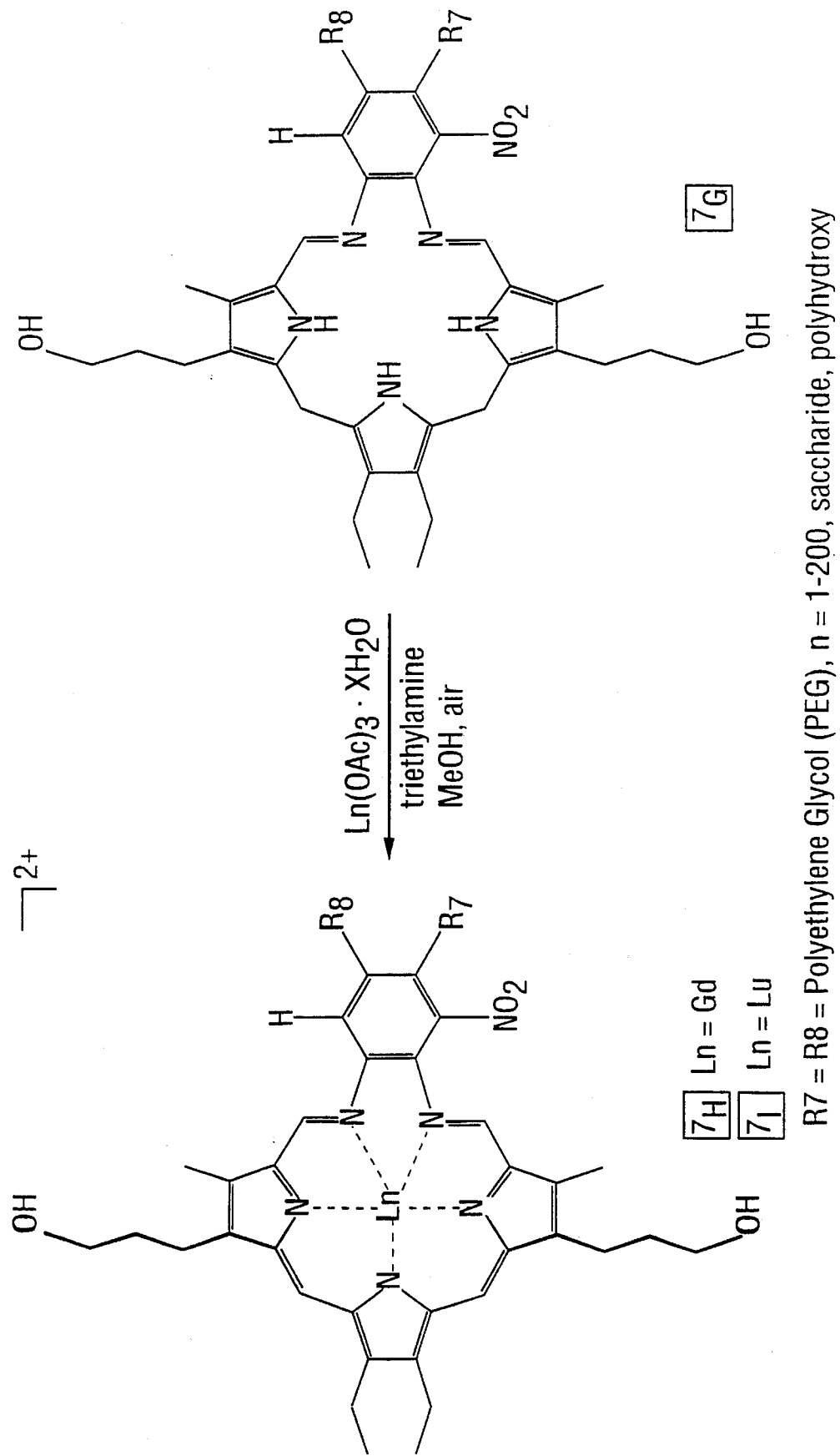

Electron withdrawing substituents may be halide other than iodide, formyl, acyl, carboxy, amide, ester or nitro. FIG. 7A and FIG. 7B show a synthetic scheme for attaching a nitro group at position $R_6$ or $R_9$. A 1,2-dialkyl-4,5-dinitrobenzene ($7_A$, also $1_A$) is reduced with ammonium formate to the diamino derivative and an amine protecting group is attached before the nitration step. Amine protecting groups include acetyl, CBZ, and carbamate, for example. An acetyl protecting group is later removed by refluxing in HCl. Protection and deprotection procedures are well known to those of skill in the art in light of the present disclosure (Greene et al. 1991). The deprotected nitro derivative $7_E$ is condensed with a diformyltripyrrane $7_F$ to form a nonaromatic texaphyrin having a nitro group at the 15 position.

A bromine is introduced at the $R_6$ and $R_9$ positions of the macrocycle by reacting 1,2-dialkyl-4,5-dinitrobenzene with bromine in the presence of $FeBr_3$ or $AlBr_3$. The 3 and 6 positions of the phenyl ring are derivatized with bromide and reduction to the amine as described in example 2 prepares the precursor for condensation with a diformyltripyrrole or a tripyrrane ketone.

Preferred texaphyrins having a substituent on the 12, 15, 18 and/or 21 position of the macrocycle are listed in Table A.

TABLE A.

Representative Substituents for Texaphyrin Macrocycles of the Present Invention

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | COOH |
| A2 | " | " | " | " | " | COOH |
| A3 | " | " | " | " | " | CONHCH-$(CH_2OH)_2$ |
| A4 | " | " | " | " | " | " |
| A5 | " | " | " | " | " | H |
| A6 | " | " | " | " | " | $OCH_3$ |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | " | " | " | " | " |
| A13 | " | " | " | " | " | $CH_3$ |
| A14 | " | " | " | " | " | " |
| A15 | " | " | " | " | " | " |
| A16 | " | " | " | " | " | " |
| A17 | " | " | " | " | $CH_3$ | H |
| A18 | " | " | " | " | " | " |
| A19 | " | " | " | " | " | " |
| A20 | $CH_2(CH_2)_2OH$ | $CH_2CH_3$ | $CH_2CH_3$ | $CH_3$ | $CH_3$ | H |
| A21 | " | " | " | " | " | " |
| A22 | " | " | " | " | " | " |
| A23 | " | " | " | " | " | " |
| A24 | " | " | " | " | " | " |
| A25 | " | " | " | " | " | " |
| A26 | " | " | " | " | " | OH |
| A27 | " | " | " | " | " | F |
| A28 | " | " | " | " | $CH_2(CH_2)_6OH$ | H |
| A29 | " | " | " | " | H | Br |
| A30 | " | " | " | " | " | $NO_2$ |
| A31 | " | " | " | " | " | COOH |

TABLE A.-continued

Representative Substituents for Texaphyrin Macrocycles of the Present Invention

| TXP | | | | | | |
|-----|---|---|---|---|---|---|
| A32 | " | " | " | " | " | $CH_3$ |
| A33 | " | " | " | " | $C_6H_5$ | H |
| A34 | " | COOH | COOH | " | $CH_2CH_3$ | " |
| A35 | " | $COOCH_2CH_3$ | $COOCH_2CH_3$ | " | $CH_3$ | " |
| A36 | $CH_2CH_2CON(CH_2CH_2OH)_2$ | $CH_2CH_3$ | $CH_2CH_3$ | " | " | " |
| A37 | $CH_2CH_2ON(CH_3)CH_2$-$(CHOH)_4CH_2OH$ | " | " | " | " | " |
| A38 | $CH_2CH_3$ | " | " | " | $CH_2(CH_2)_6OH$ | " |

| TXP | $R_7$ | $R_8$ | $R_9$ | $R_{10}$ |
|-----|-------|-------|-------|----------|
| A1  | $O(CH_2)_3OH$ | $O(CH_2)_3OH$ | $O(CH_2)_3OH$ | H |
| A2  | $O(CH_2CH_2O)_3CH_3$ | $O(CH_2CH_2O)_3CH_3$ | COOH | " |
| A3  | $O(CH_2CH_2O)_3CH_3$ | $O(CH_2CH_2O)_3CH_3$ | O-saccharide | " |
| A4  | " | " | $O(CH_2CH_2O)_3CH_3$ | " |
| A5  | " | $O(CH_2)_3CON$-linker-oligo | " | " |
| A6  | H | $OCH_2CON$-linker-oligo | $OCH_3$ | " |
| A7  | " | $OCH_2CO$-poly-L-lysine | " | " |
| A8  | " | $OCH_2CO$-estradiol | " | " |
| A9  | " | $O(CH_2CH_2O)_3CH_3$ | " | " |
| A10 | $O(CH_2CH_2O)_3CH_3$ | " | " | " |
| A11 | " | $OCH_2CON$-linker-oligo | " | " |
| A12 | " | $OCH_2CO$-estradiol | " | " |
| A13 | " | $O(CH_2CH_2O)_3CH_3$ | $O(CH_2CH_2O)_3CH_3$ | " |
| A14 | " | $OCH_2CO$-estradiol | " | " |
| A15 | $O(CH_2CH_2O)_3CH_3$ | $O(CH_2CH_2O)_{120}CH_3$ | $OCH_3$ | " |
| A16 | H | saccharide | " | " |
| A17 | $O(CH_2)_3OH$ | $O(CH_2)_3OH$ | H | $CH_3$ |
| A18 | H | $O(CH_2CH_2O)_3CH_3$ | " | " |
| A19 | $O(CH_2CH_2O)_3CH_3$ | " | " | " |
| A20 | H | $OCH_2CON$-linker-oligo | H | $CH_3$ |
| A21 | " | $OCH_2CO$-estradiol | " | " |
| A22 | " | $OCH_2CON(CH_2CH_2OH)_2$ | " | " |
| A23 | $O(CH_2CH_2O)_3CH_3$ | $O(CH_2CH_2O)_{120}CH_3$ | " | " |
| A24 | " | $OCH_2CON$-linker-oligo | " | " |
| A25 | H | $CH_2CON(CH_3)CH_2$-$(CHOH)_4CH_2OH$ | " | " |
| A26 | $O(CH_2CH_2O)_3CH_3$ | $O(CH_2CH_2O)_3CH_3$ | OH | " |
| A27 | " | " | F | " |
| A28 | " | " | H | $CH_2(CH_2)_6OH$ |
| A29 | " | " | Br | H |
| A30 | " | " | $NO_2$ | " |
| A31 | " | " | COOH | " |
| A32 | " | " | $CH_3$ | " |
| A33 | " | " | H | $C_6H_5$ |
| A34 | " | " | " | $CH_2CH_3$ |
| A35 | " | " | " | $CH_3$ |
| A36 | " | " | " | " |
| A37 | $OCH_3$ | $OCH_3$ | " | " |
| A38 | H | $OCH_2CO_2$-glucosamine | " | $CH_2(CH_2)_6OH$ |

A substituent on the $R_5$ or $R_{10}$ position of the macrocycle may be derivatized after condensation of the macrocycle. Substituents may include an alkyl group having up to 5 carbon atoms or a phenyl group which may be further derivatized with a nitro, carboxyl, sulfonic acid, hydroxyl, halide or alkoxy where the alkyl of the alkoxy may be hydroxyalkyl and like, as described in U.S. Pat. No. 5,252,720 and application Ser. No. 08/135,118.

EXAMPLE 5

Further Derivatives of Texaphyrin

One skilled in the art of organic synthesis in light of the present disclosure could extend and refine the basic synthetic chemistry outlined in this application, in U.S. Pat. No. 5,252,720 and in application Ser. No. 08/135,118 so as to produce texaphyrins having various substituents, yet having basic utility to those specifically detailed in the present examples. For example, polyether-linked polyhydroxylated groups, catechol (i.e. benzene diol) derivatives bearing further hydroxyalkyl substituents off the tripyrrane-derived portion of the macrocycle, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride or p-nitrophenol acetate would generate activated acyl species suitable for attachment to monoclonal antibodies or other biomolecules of interest. Standard in situ coupling methods (e.g. 1,1'-carbonyldiimidazole (CDI)) could be used to effect the conjugation.

The selectivity of the texaphyrins may be enhanced by covalently linking oligonucleotides onto the periphery of the macrocycle. Amides, ethers and thioethers are representative of linkages which may be used for this purpose. Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligodeoxynucleotide-complex conjugates may be designed so as to provide optimal catalytic interaction between a target nucleic acid and the bound texaphyrin. The oligonucleotide may be large enough to bind probably at least 15 nucleotides of complementary nucleic acid.

A general method for preparing oligonucleotides of various lengths and sequences is described by Caracciolo et al. (1989). Preferred oligonucleotides resistant to in vivo hydrolysis may contain a phosphorothioate substitution at each base (*J. Org. Chem.*, 55:4693–4699, 1990). Oligodeoxynucleotides or their phosphorothioate analogues may be synthesized using an Applied Biosystem 380B DNA synthesizer (Applied Biosystems, Inc., Foster City, Calif.).

Another means of gaining selectivity may be to covalently link the texaphyrin complex to a sapphyrin (sap) molecule, (U.S. Pat. No. 5,159,065; U.S. Pat. No. 5,120,411; U.S. Pat. No. 5,041,078, all incorporated by reference herein.) Since sapphyrins bind DNA, K~$10^6$ M$^{-1}$, (U.S. Ser. No. 07/964,607, incorporated by reference herein) the linked texaphyrin-sapphyrin complex (txph-sap) could effectively increase the texaphyrin concentration at locations adjacent to the sapphyrin binding sites. Sapphyrins have a higher fluorescent quantum yield than texaphyrins, allowing greater fluorescence detection. A laser system may be employed where the molecules are optimized to the laser wavelength; an excited sapphyrin may transfer its energy to the conjugated texaphyrin for detection. The texaphyrin molecule may further be designed to pass through cell membranes for selective radiosensitization.

New texaphyrin derivatives are characterized fully using normal spectroscopic and analytical means, including, X-ray diffraction methods. Water solubility for a new texaphyrin metal complex may be determined as follows. A saturated solution of GdTXP, for example, in water or 5% mannitol is placed into a centrifuge tube, shaken vigorously and centrifuged at about 12,000 rpm for about 1–2 hours. The tube is held for about 24 hours for equilibration after which the supernatant is decanted and filtered through a 0.2µ membrane. The absorbance of the filtrate diluted in methanol is determined at about 470–475 nm where the Sorer-like band has its maximum. The extinction coefficient or molar absorptivity ($\epsilon$) is 117426 M$^{-1}$cm$^{-1}$ at 474 nm for GdT2B2 and 114630 M$^{-1}$cm$^{-1}$ at 473 nm for GdT2B2Peg (T2B2 with polyethyleneglycol-like R groups on R$_7$ and R$_8$). The use of these molar absorptivities would give a value for concentration of a new texaphyrin metal complex with an error of about 10%.

A means for determining whether a new texaphyrin retains lipophilicity may be carried out by a partitioning of the metallotexaphyrin in organic/aqueous media. In several glass vortex tubes, a 3 mL solution of a metallotexaphyrin (16 µg/mL) in 5% aqueous mannitol is combined with increasing concentrations of cholesterol (0–80%) in chloroform (3 mL). The two phase mixture is vortexed for a few minutes and then the two layers are allowed to separate. The resulting concentration of metallotexaphyrin in each layer is measured by the optical spectrum (i.e., molar absorptivity, $\epsilon$). From this data, a plot may be generated of the ratio of a metallotexaphyrin in the organic phase/aqueous phase vs. % cholesterol. A texaphyrin having some solubility in the cholesterol/chloroform solution has retained lipophilicity.

A complete analysis of the optical properties may be made for new systems under a range of experimental conditions including conditions designed to approximate those in vivo. Detailed analyses, including triplet lifetime and singlet oxygen quantum yield determinations may be made. The objective is to obtain a complete ground and excited state reactivity profile for each new texaphyrin produced. Questions such as when singlet oxygen production is maximized, how the quantum yield for its formation is influenced by the position of the lowest energy (Q-type) transition, whether aggregation is more prevalent in certain solvents or in the presence of certain biologically important components (e.g. lipids, proteins, etc.), and, finally, whether significant differences in in vitro optical properties are derived from the use of elaborated texaphyrins bearing cationic, anionic, or neutral substituents may be answered.

With newly prepared complexes, screening experiments are carried out. Standard in vitro protocols are used to evaluate the in vitro photo-killing ability of the texaphyrin derivatives in question. For instance, the texaphyrin complexes of choice may be administered in varying concentrations to a variety of cancerous cells and the rate of cell replication determined both in the presence and absence of light. Similarly, texaphyrin complexes of choice may be added to standard viral cultures and the rate of viral growth retardation determined in the presence and absence of light. A variety of solubilizing carriers will be used to augment the solubility and/or monomeric nature of the texaphyrin photosensitizers and the effect, if any, that these carriers have in adjusting the biodistribution properties of the dyes will be assessed (using primarily fluorescence spectroscopy). Appropriate control experiments are carried out with normal cells so that the intrinsic dark and light toxicity of the texaphyrins may be determined.

From a generalized set of in vitro experimental procedures, a clear picture of the photodynamic capabilities of the texaphyrin derivatives will emerge. Preliminary toxicity and stability information will result from the in vitro experiments. Particular questions of interest include the half-life of texaphyrin derivatives under physiological conditions, whether the nature of the central metal influences stability and whether the central cation is affecting cytotoxicity. It is not possible to remove the larger bound cations (e.g. Cd$^{2+}$ or Gd$^{3+}$) by simple chemical means (Zn$^{2+}$, however, appears to "fall out" with ease). Preliminary results indicate that the lanthanum(III)-containing texaphyrin complex is not appreciably cytotoxic. Nonetheless, the question of intrinsic toxicity is one of such central importance that the cytotoxicity of all new systems should be screened in vitro and, where appropriate, further in vivo toxicity studies carried out.

EXAMPLE 6

Viral Inactivation by Texaphyrin Macrocycles

One aspect of the utility of the present invention is the use of complexes described herein for photon-induced deactivation of viruses and virally infected or potentially infected eucaryotic cells. U.S. Pat. No. 5,252,720 teaches investigations of the photosensitized inactivation of peripheral mononuclear cells and enveloped viruses, in particular, Herpes Simplex Virus, Type 1 (HSV-1) in culture medium using various texaphyrins.

As reported in a parent application, two cadmium-containing texaphyrins at concentrations of 20 μM demonstrated ≈90% viral inactivation as judged by viral plaque assay. As shown by mitogenic assay, aerobic photosensitization of cells exposed to a texaphyrin-cadmium complex at 0.15 μM and 20 joules/cm$^2$ of 770 nm wavelength light caused significant inhibition of the cellular division of PMC's.

Texaphyrins having electron donating substituents in the 12, 15, 18 and/or 21 positions of the macrocycle and having resultant greater hydrolyric stability compared to texaphyrins of the parent application are expected to be more effective photosensitizers for the destruction of free enveloped viruses such as HIV-1, virally-infected peripheral mononuclear cells, leukemia or lymphoma cells contaminating bone-marrow, for example.

EXAMPLE 7

Antibody Directed and Intrinsic Biolocalization

U.S. Pat. No. 5,252,720 teaches using a texaphyrin bifunctional conjugate for use in radioisotope-based diagnostics and in radioisotope-based therapy. The texaphyrin molecules of the present invention are especially suited for acting as bifunctional chelating agents in antibody conjugate-based treatment since they have greater hydrolyric stability compared to the compounds of the parent application, they have functional groups suitable for conjugation to the antibody, they form covalent linkages that are stable in vivo which do not destroy the immunological competence of the antibody, they are relatively nontoxic, and they are readily soluble in a physiological environment. A further advantage of these texaphyrins is that they are suitable for further functionalization.

The ability to attach and deliver a potent photosensitizer directly to a tumor locus could have tremendous potential benefit in the treatment of neoplastic disorders. In addition, this approach will allow a variety of useful radioisotopes such as and $^{111}$In to be attached to a monoclonal antibody for specific targeting.

The texaphyrin molecules of the present invention are also suited for delivering radioactivity to a tumor on their own since they chelate radioisotopes and have intrinsic biolocalization selectivity.

EXAMPLE 8

Texaphyrins as an Internal Radioactive Source

Radioisotopes play a central role in the detection and treatment of neoplastic disorders. Improving their efficacy in medical applications involves attaching radioisotopes to tumor-directed molecules. For example, radiolabeled antibodies could serve as "magic bullets" and allow the direct transport of radioisotopes to neoplastic sites thus minimizing whole body exposure to radiation. The use of bifunctional metal chelating agents in radioimmunodiagnostics (RID), radiosensitization and therapy (RIT) is most closely related to texaphyrins of the present invention having greater hydrolyric stability than those described previously. In these procedures, the radiometal of interest must be bound and retained under physiological conditions. The potential damage arising from "free" radioisotopes, released from the complex, can be very serious. The advantage of a chelate, such as a texaphyrin metal complex, that does not allow for metal release is clear.

For the purposes of imaging, an ideal isotope should be readily detectable by available monitoring techniques and induce a minimal radiation-based toxic response. In practice, these and other necessary requirements implicate the use of a γ-ray emitter in the 100 to 250 KeV range, which possesses a short effective half-life (biological and/or nuclear), decays to stable products, and, of course, is readily available under clinical conditions. To date, therefore, most attention has focused on $^{131}$I ($t_{1/2}$=193h), $^{123}$I ($t_{1/2}$=13h), $^{99m}$Tc($t_{1/2}$=6.0 h), $^{67}$Ga($t_{1/2}$=78h), and $^{111}$In($t_{1/2}$=67.4h) which come closest to meeting these criteria. Each of these enjoys advantages and disadvantages with respect to antibody labeling for RID; these aspects are discussed in parent patent application Ser. No. 08/135,118. Texaphyrin forms a kinetically and hydrolytically stable complex with In$^{3+}$; such a ligand system may be elaborated and serve as the critical core of a bifunctional conjugate for use in $^{111}$In-based radioimmunodiagnostics.

Many of the same considerations hold true for radioisotope-based therapy as do for radioisotope-based diagnostics. A number of β emitters, including $^{131}$I, are currently receiving attention as possible candidates for RIT. Among the more promising, are $^{186}$Re ($t_{1/2}$=90 h, $^{67}$Cu ($t_{1/2}$=58.5 h), and $^{90}$Y ($t_{1/2}$=65 h). Of these, $^{90}$Y is considered the best, with an emission energy of 2.28 MeV, it is calculated to deliver roughly 3 to 4 times more energy (dose) to the tumor per nanomole than either $^{186}$Re or $^{67}$Cu. A texaphyrin-type bifunctional conjugate may be prepared for use in $^{90}$Y-based RIT. $^{90}$Y may be attached to an antibody of choice using a functionalized texaphyrin.

The Y$^{3+}$ and In$^{3+}$ complexes of texaphyrin are formed rapidly (insertion and oxidation times are less than 3 hours) from the methylene-linked reduced precursor, and have a half-life of about 3 weeks in 1:1 methanol-water mixtures. $^{153}$Gd is primarily a gamma emitter and is a preferred paramagnetic metal for magnetic resonance imaging. $^{153}$GdB2T2 localizes to the liver and would be a preferred metal complex for use as a tracer for pharmacokinetic studies. Texaphyrins having electron donating groups on the 12, 15, 18 and/or 21 positions of the present invention are particularly suited for this application due to their enhanced stability. A texaphyrin complexed to $^{90}$Y may be administered in combination with another texaphyrin complexed to a diamagnetic metal for photodynamic tumor therapy, for example, to achieve a synergistic killing of malignant cells.

EXAMPLE 9

Texaphyrins for Magnetic Resonance Imaging

According to U.S. Pat. No. 5,252,720, nonlabile Gd(III) complexes of hydroxy-substituted texaphyrins are useful contrast agents for MRI applications. Rats bearing subcutaneously implanted methylcholanthrene-induced fibrosarcomas in their left flanks (n=4) were studied for imaging. Standardized signal intensities (SSI) increased in liver by 81.7%, kidney by 114.9% and tumor by 49.7% from pre- to 10–15 minutes post-contrast. These results show that the T2B2 gadolinium complex is an hepatic, renal and tumor-specific contrast agent. The agent was found to have relatively low toxicity in rodents. Tumor enhancement persisted for up to 28 hours.

Also in the above-cited patent, selective labeling of endothelial cell surface and atheromas plaque relative to surrounding tissue was observed in human cadaveric aorta. These data indicate that the Gd(III)B2T2 complex has utility in the non-invasive imaging of atheroma. The gadolinium complex of B2T2 also shows accumulation in the upper GI tract, especially the stomach, as determined by magnetic resonance imaging.

Imaging of a carcinoma implanted in rabbit thigh muscle using Gd(III)B2T2 was reported in parent application, Ser. No. 08/135,118. Image enhancement was achieved at doses as low as 5 μmol/kg and viable liver image augmentation was obtained when using doses as low as 2 μmol/kg. Gd(III)B2T2 was able to localize in hypoxic areas of tumors.

Standard radiowave protons are used for magnetic resonance imaging, however, photons in several regions of the electromagnetic spectrum are suitable for medical imaging. Gamma-ray photons are used for position emission tomography (PET) and single-photon emission computed tomography (SPECT); x-ray photons are used for conventional radiography, computed tomography, digital subtraction angiography (DSA) and iodine K-edge dichromography (ID). The use of internal x-ray emitting isotopes is discussed in Example 8.

EXAMPLE 10

Radiation Sensitization of Tumor Cells Using Gadolinium Texaphyrin

Parent application U.S. Ser. No. 08/135,118 teaches the use of texaphyrins as radiosensitizers to enhance the effect of radiation therapy.

The damaging effects of radiation therapy are mediated by the radiation products of water, in particular, the hydroxyl radical and solvated electrons. The hydroxyl radical is an oxidizing radical and primarily responsible for radiation damage. The radical is extremely reactive and short lived. It causes damage primarily in the vicinity in which it is generated and if it comes in contact with a solvated electron, it will be neutralized. Solvated electrons are strong reducing radicals and highly energetic particles. They are very small by comparison to the hydroxyl radical and travel great distances quickly. They will neutralize hydroxyl radicals readily. Therefore, one of the mechanisms of a radiosensitizer is to "soak up" solvated electrons and prevent them from neutralizing hydroxyl radicals, thereby, allowing hydroxyl radicals to do their damage.

Texaphyrins of the present invention having electron withdrawing substituents attached to the 15 and/or 18 positions are more readily reduced due to destabilization of the aromatic π system. These texaphyrins are particularly useful in radiosensitization since they more easily gain an electron to form a radical as compared to those texaphyrins previously described. Such electron withdrawing groups include halide other than iodide, formyl, acyl, carboxy, nitro substituents and the like. Texaphyrins have the following advantageous properties for use as a radiosensitizer:

i) low redox potential of GdTXP causes solvated electrons to flow to GdTXP, allowing hydroxyl radicals to do their damage, ii) the texaphyrin radical is relatively stable, yet reacts readily to covalently modify neighboring molecules, and iii) texaphyrin may be particularly effective for treating the hypoxic areas of solid tumors because of intrinsic biolocalization and its indifference to the presence of $O_2$.

The advantageous low redox potential of gadolinium texaphyrin confers a degree of specificity to radiation damage using texaphyrin; in the absence of texaphyrin, hydroxyl radicals and solvated electrons recombine and little radiation damage occurs, in the presence of texaphyrin, hydroxyl radicals are free to do their damage. Furthermore, the trapping of electrons by texaphyrin prevents the solvated electrons from interacting with the hydroxyl radical-induced damage site to repair the damage.

Parent application Ser. No. 08/135,118 presents data which demonstrate formation of the gadolinium texaphyrin anion, $GdTX^{-\bullet}$, the decay of the anion, data which show that the TXP anion has a lower reduction potential than oxygen and therefore does not pass its electrons to oxygen, covalent modification of cytosine by a texaphyrin radical, the killing of mouse L1210 cells in the presence of 20 μM GdTXP and the effect of GdTXP on nucleic acid strand scission under radiolysis. The presence of a metal is not necessary for the radiosensitization properties of texaphyrins, however, the metal contributes stability to the texaphyrin complex.

The radiosensitization properties of the texaphyrins described herein may allow reduced doses of radiation to be effective in treatment of an individual. Therefore, radiation side effects such as nausea and damage to normal cells may be lessened when treatment includes the use of texaphyrins of the present invention. Expected dose levels for an individual may range from 2–8 mg/kg administered for a period of 2 to 24 hours.

EXAMPLE 11

Photodynamic Therapy

U.S. Pat. No. 5,252,720 demonstrates results which show that La(III)B2T2 is phototoxic to murine mammary carcinoma cells in vitro and to murine adenocarcinoma tumor masses in Balb/c mice in vivo. Texaphyrins may be conjugated to biological molecules, especially proteins of molecular weight greater than about 20,000 daltons, e.g. albumin and gamma globulin, in order to slow their clearance by the kidneys. For photodynamic tumor therapy, a prolonged presence of these complexes in tissue may be desirable for photoirradiation purposes. The conjugation would be accomplished as described in Example 7 for antibody conjugates. The parent application also teaches the use of texaphyrins for localization by magnetic resonance imaging followed by photodynamic therapy for treatment of a tumor.

The texaphyrins of the present invention, due to their greater hydrolyric stability, are especially appropriate candidates for localization by MRI, photodynamic tumor treatment and for the combined diagnosis and treatment discussed in the parent application.

EXAMPLE 12

Texaphyrins for Radiosensitization and Localization followed by Radiotherapy and/or Photodynamic Tumor Therapy for Tumor Destruction This example describes the use of texaphyrins in the localization, radiosensitization and destruction of tumor tissue. A texaphyrin is administered to a host harboring benign or malignant tumor cells. The texaphyrin exhibits radiosensitization properties and selective biolocalization in benign or malignant tumor cells relative to surrounding tissue. Localization sites in the host are determined by reference to the texaphyrin using, for example, magnetic resonance imaging when a paramagnetic metal complex of texaphyrin is administered, fluorescence when a free-base texaphyrin is administered, or gamma body scanning when a gamma-emitting metal is complexed with the administered texaphyrin. A preferred paramagnetic metal is Gd(III).

The inherent radiosensitization properties of the texaphyrins as described in Example 10 allow electromagnetic radiation to be more effective and selective when administered in the vicinity of the texaphyrin metal complex. Lower doses of radiation may therefore be used. The radiation may be from an external source or may be from an internal source, such as a radiometal bound to a texaphyrin. Examples of a radiometal include $^{153}$Gd, $^{111}$In, or $^{90}$Y. Alternatively, a second texaphyrin metal complex having essentially identical biolocalization property and exhibiting the ability to generate singlet oxygen upon exposure to light is administered. The second texaphyrin metal complex is photoirradiated in proximity to the benign or malignant tumor cells, as in fiber optics, to cause tumor tissue destruction from the singlet oxygen produced. The detectable metal in the second texaphyrin metal complex is a diamagnetic metal, preferably La(III), Lu(III) or In(III).

A further embodiment is the use of a texaphyrin radiosensitizer and a photosensitive texaphyrin for treatment. This molecule may be a single texaphyrin metal diamagnetic complex. A synergistic killing of cells may then be achieved by the use of light for photodynamic therapy in combination with electromagnetic radiation. An alternative embodiment is a synergistic killing due to an intrinsic radiochelated texaphyrin and externally applied radiation. In vitro uses of the method of radiosensitization and radiation therapy include sterilizations, and in the treatment of bone marrow, transfused blood or transplanted organs.

Texaphyrin-metal complexes will be chosen which themselves show a high intrinsic biolocalization selectivity for tumors or neoplastic tissues. For example, the B2T2 Gd(III) complex demonstrates in vivo affinity for tissue high in lipid content, atheroma, the liver, kidneys and tumors.

Texaphyrin complexes are good candidates for such biomedical radiosensitizers and photosensitizers. They "soak up" electrons in an irradiated area, allowing hydroxyl radicals to cause radiation damage; texaphyrin radicals react covalently with neighboring molecules causing further radiation damage, they are easily available, have low intrinsic cytotoxicity, long wavelength absorption, generate singlet oxygen, are soluble in physiological environments, have the ability to be conjugated to site specific transport molecules, have quick elimination, are stable and are easily subject to synthetic modification. Significant advantages to using texaphyrins for imaging and destruction of cells are i) one texaphyrin is used for both functions, ii) the inherent selective biolocalization and the potential for derivatization to enhance further localization, iii) due to the radiosensitization properties of texaphyrin, radiation is more effective and lower doses of radiation may be used, therefore, fewer side effects are experienced and iv) a metal complex is not necessary for radiosensitization. The present invention provides a method to "see" and "kill" particular cells with a single agent having biolocalization selectivity and radiation enhancing properties.

The following references and those cited herein are incorporated in pertinent part by reference herein for the reasons cited below.

REFERENCES

U.S. Ser. No. 07/964,607
U.S. Ser. No. 08/098,514
U.S. Ser. No. 08/135,118
U.S. Pat. No. 4,935,498
U.S. Pat. No. 5,041,078
U.S. Pat. No. 5,120,411
U.S. Pat. No. 5,159,065
U.S. Pat. No. 5,162,509
U.S. Pat. No. 5,252,720
U.S. Pat. No. 5,256,399
U.S. Pat. No. 5,272,142
Aramendia et al. (1986) *Photochem. Photobiol.*, 44:555.
Bauer et al. (1983) *J. Am. Chem. Soc.* 105:6429–6436.
Broadhurst et al. (1972) *J. Chem. Soc. Perkin Trans.* 1:2111–2116.
Caracciolo et al. (1989) *Science*, 245:1107
Gosmann et al. (1986) *Angew. Chem.*, 98:1107.
Greene et al. (1991) Protective Groups in Organic Synthesis, John Wiley & Sons Inc., 2nd ed., Chapter 7.
Harriman et al. (1989) *J. Chem. Soc., Chem. Commun.*, 5:314.
Kaesler et al. (1983) *J. Chem. Soc.*, 48:4399–4401.
LeGoff et al. (1987) *J. Org. Chem.*, 710–711.
Vogel et al. (1990) *Angew. Chem. Int. Ed. Eng.*, 29:1387.
Vogel et al. (1986) *Angew. Chem.*, 98:262.
Vogel et al. (1987) *Angew. Chem. Int. Ed. Eng.*, 26:928.
*J. Org. Chem.*, 55:4693–4699, (1990)

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A texaphyrin having the structure:

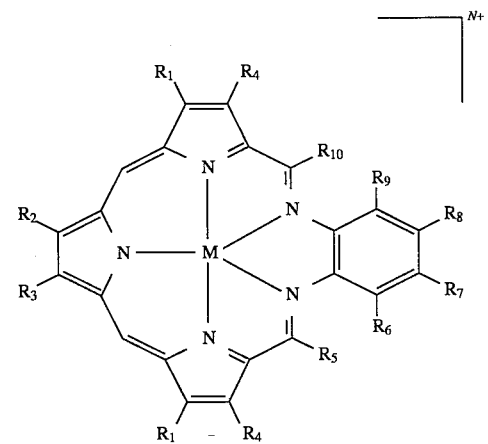

wherein

M is H, a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2^{+2}$ or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$;

$R_1$–$R_4$ and $R_6$–$R_9$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, carboxy, carboxyalkyl, carboxyamidealkyl, a sapphyrin molecule, or a linker to a sapphyrin molecule;

$R_5$ and $R_{10}$ are independently hydrogen, alkyl, aryl, hydroxyalkyl, oxyalkyl, oxyhydroxyalkyl, carboxyalkyl, carboxyamidealkyl or a linker to a sapphyrin molecule;

at least one of $R_5$, $R_6$, $R_9$, and $R_{10}$ is other than hydrogen; and

N is an integer less than or equal to 2.

2. The texaphyrin of claim 1 wherein:

$R_1$–$R_4$ and $R_6$–$R_9$ are independently hydrogen, hydroxyl, alkyl, aryl, hydroxyalkyl, oxyalkyl, oxyhydroxyalkyl, carboxyalkyl, carboxyamidealkyl, a sapphyrin molecule, or a linker to a sapphyrin molecule; and $R_5$ and $R_{10}$ are independently hydrogen, alkyl, aryl, hydroxyalkyl, oxyalkyl, oxyhydroxyalkyl, carboxyalkyl, carboxyamidealkyl or a linker to a sapphyrin molecule.

3. The texaphyrin of claim 1 wherein:

$R_1$–$R_4$, $R_7$ and $R_8$ are independently hydrogen, halide other than iodide, hydroxyl, alkyl, aryl, haloalkyl, nitro, formyl, acyl, hydroxyalkyl, oxyalkyl, oxyhydroxyalkyl, carboxy, carboxyalkyl, carboxyamidealkyl, a sapphyrin molecule, or a linker to a sapphyrin molecule;

$R_5$ and $R_{10}$ are independently hydrogen, alkyl, aryl, hydroxyalkyl, oxyalkyl, oxyhydroxyalkyl, carboxyalkyl, carboxyamidealkyl or a linker to a sapphyrin molecule;

$R_6$ and $R_9$ are independently halide other than iodide, formyl, acyl, carboxy, or nitro; and at least one of $R_6$ and $R_9$ is other than hydrogen.

4. The texaphyrin of claim 1 further defined as being water soluble.

5. The texaphyrin of claim 1 wherein the halide other than iodide is fluoride, chloride or bromide.

6. The texaphyrin of claim 1 wherein the alkyl, aryl, hydroxyalkyl, oxyalkyl, oxyhydroxyalkyl, carboxyalkyl, carboxyamidealkyl or sapphyrin molecule is covalently bonded to the texaphyrin via a carbon-carbon or a carbon-oxygen bond.

7. The texaphyrin of claim 1 wherein the aryl is a phenyl substituent.

8. The texaphyrin of claim 1 wherein the aryl is phenyl having a nitro, carboxy, sulfonic acid, hydroxy, oxyalkyl or halide other than iodide substituent.

9. The texaphyrin of claim 1 wherein the oxyhydroxyalkyl is alkyl having independently hydroxy substituents and ether branches.

10. The texaphyrin of claim 1 wherein the oxyhydroxyalkyl is $C_{(n-x)}H_{((2n+1)-2x)}O_xO_y$ or $OC_{(n-x)}H_{((2n+1)-2x)}O_xO_y$ where n is a positive integer from 1 to 10;

x is zero or a positive integer less than or equal to n; and y is zero or a positive integer less than or equal to $((2n+1)-2x)$.

11. The texaphyrin of claim 1 wherein the oxyhydroxyalkyl is $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to $2n+1$, $R^a$ is independently H, alkyl, hydroxyalkyl, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$, where m is a positive integer from 1 to 10, z is zero or a positive integer less than $((2m+1)-r)$, r is zero or a positive integer less than or equal to $2m+1$, and $R^b$ is independently H, alkyl or hydroxyalkyl.

12. The texaphyrin of claim 1 wherein the carboxyamidealkyl is alkyl having secondary or tertiary amide linkages.

13. The texaphyrin of claim 1 wherein the carboxyamidealkyl is $(CH_2)_nCONHR^a$, $O(CH_2)_nCONHR^a$, $(CH_2)_nCON(R^a)_2$, or $O(CH_2)_aCON(R^a)_2$ where n is a positive integer from 1 to 10, $R^a$ is independently H, alkyl, hydroxyalkyl, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$, where m is a positive integer from 1 to 10, z is zero or a positive integer less than $((2m+1)-r)$, r is zero or a positive integer less than or equal to $2m+1$, and $R^b$ is independently H, alkyl or hydroxyalkyl.

14. The texaphyrin of claim 1 wherein the carboxyalkyl is alkyl having a carboxyl substituted ether, an amide substituted ether or a tertiary amide removed from an ether.

15. The texaphyrin of claim 1 wherein the carboxyalkyl is $C_nH_{((2n+1)-q)}O_yR^c_q$ or $OC_nH_{((2n+1)-q)}O_yR^c_q$ where n is a positive integer from 1 to 10;

y is zero or a positive integer less than $((2n+1)-q)$, q is zero or a positive integer less than or equal to $2n+1$, $R^c$ is $(CH_2)_nCO_2R^d$, $(CH_2)_nCONHR^d$ or $(CH_2)_nCON(R^d)_2$ where n is a positive integer from 1 to 10;

$R^d$ is independently H, alkyl, hydroxyalkyl, $C_{(m-w)}H_{((2m+1)-2w)}O_wO_z$, $O_2C_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$, where m is a positive integer from 1 to 10, z is zero or a positive integer less than $((2m+1)-r)$, r is zero or a positive integer less than or equal to $2m+1$, and $R^b$ is independently H, alkyl or hydroxyalkyl.

16. The texaphyrin of claim 1 wherein the linker is an amide, thiol, thioether or ether covalent bond.

17. The texaphyrin of claim 1 wherein the sapphyrin has binding specificity for localization to a treatment site.

18. The texaphyrin of claim 1 wherein $R_1$–$R_4$, $R_7$ and $R_8$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, carboxy, carboxyalkyl, carboxyamidealkyl, a sapphyrin molecule, or a linker to a sapphyrin molecule;

at least one of $R_5$ and $R_{10}$ is alkyl, aryl, hydroxyalkyl, oxyalkyl, oxyhydroxyalkyl, carboxyalkyl, carboxyamidealkyl or a linker to a sapphyrin molecule;

where $R_5$ is other than hydrogen, then $R_6$ is hydrogen, fluorine or hydroxyl; and where $R_{10}$ is other than hydrogen, then $R_9$ is hydrogen, fluorine or hydroxyl.

19. The texaphyrin of claim 1 wherein $R_1$–$R_4$, $R_7$ and $R_8$ are independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, carboxy, carboxyalkyl, carboxyamidealkyl, a sapphyrin molecule, or a linker to a sapphyrin molecule;

at least one of $R_6$ and $R_9$ is halide other than iodide, hydroxyl, alkyl, aryl, haloalkyl other than iodoalkyl, nitro, formyl, acyl, hydroxyalkyl, oxyalkyl, oxyhydroxyalkyl, carboxy, carboxyalkyl, carboxyamidealkyl, a sapphyrin molecule, or a linker to a sapphyrin molecule;

where $R_6$ is other than hydrogen, then $R_5$ is hydrogen or methyl; and where $R_9$ is other than hydrogen, then $R_{10}$ is hydrogen or methyl.

20. The texaphyrin of claim 1 where $R_2$ and $R_3$ are $CH_2CH_3$ and $R_4$ is $CH_3$.

21. The texaphyrin of claim 1 where $R_5$ and $R_{10}$ are methyl.

22. The texaphyrin of claim 1 where $R_5$ and $R_{10}$ are $CH_2(CH_2)_6OH$.

23. The texaphyrin of claim 1 where $R_5$ and $R_{10}$ are $(CH_2)_nCH_3$ where n is 0, 1, 2, 3 or 4.

24. The texaphyrin of claim 1 where $R_5$ and $R_{10}$ are phenyl having an $R_{11}$ substituent where $R_{11}$ is hydrogen, nitro, carboxy, sulfonic acid, hydroxy, oxyalkyl or halide other than iodide.

25. The texaphyrin of claim 1 where $R_6$ is carboxy.

26. The texaphyrin of claim 1 where $R_6$ is alkyl or oxyalkyl.

27. The texaphyrin of claim 1 where $R_6$ is hydroxyl, halide other than iodide or nitro.

28. The texaphyrin of claim 1 where $R_6$ is carboxyamidealkyl having a tertiary amide linkage.

29. The texaphyrin of claim 1 wherein $R_1$ is $CH_2(CH_2)_2OH$.

30. The texaphyrin of claim 1 wherein $R_7$ or $R_8$ is $O(CH_2CH_2O)_3CH_3$.

31. The texaphyrin of claim 1 wherein $R_8$ is any one of the substituents listed for $R_8$ in Table A.

32. The texaphyrin of claim 1 wherein $R_9$ is any one of the substituents listed for $R_9$ in Table A.

33. The texaphyrin of claim 1 wherein $R_1$–$_{10}$ are as in Table A for texaphyrins A1–A38.

34. The texaphyrin of claim 1 wherein $R_1$ is $CH_2(CH_2)_2OH$, $R_2$ and $R_3$ are $CH_2CH_3$, $R_4$, $R_5$ and $R_{10}$ are $CH_3$, $R_6$ and $R_9$ are H and $R_7$ and $R_8$ are $O(CH_2CH_2O)_3CH_3$.

* * * * *

UNITED STATES PATENT AND TRADEMARK OFFICE
CERTIFICATE OF CORRECTION

PATENT NO. : 5,599,923

DATED : February 4, 1997

INVENTOR(S) : Sessler et al.

It is certified that error appears in the above-identified patent and that said Letters Patent is hereby corrected as shown below:

In claim 1, column 30, line 67, please delete "U+$^3$" and insert -- $U^{+3}$ -- therefor.

In claim 11, column 32, line 9, please delete "$C_mH_{((2m+1)-r)}O_zR^b_r$," and insert -- $C_mH_{((2m+1)-r)}O_zR^b_r$ -- therefor.

In claim 13, column 32, line 20, please delete $O(CH_2)_aCON(R^a)_2$" and insert -- $O(CH_2)_nCON(R^a)_2$ -- therefor.

In claim 33, column 34, line 26, please delete "$R_{1-10}$" and insert -- $R_1$-$R_{10}$ -- therefor.

Signed and Sealed this

Twenty-ninth Day of July, 1997

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,599,923
DATED : February 4, 1997
INVENTOR(S) : Sessler, et. al.

It is certified that error appears in the above-identified patent and that said Letters Patent is hereby corrected as shown below:

At column 1, immediately following the title, please replace lines 4 – 6 with:

-- The government may own certain rights in the present invention pursuant to one or more of the following: National Institutes of Health Grants CA68682, AI28845 and AI33577; and National Science Foundation Grants CHE8552768 and CHE9122161.--

Signed and Sealed this

Thirtieth Day of May, 2000

Attest:

Q. TODD DICKINSON

*Attesting Officer*  *Director of Patents and Trademarks*